(12) United States Patent
Wojcik

(10) Patent No.: US 9,789,030 B2
(45) Date of Patent: Oct. 17, 2017

(54) SKIN PORT CONNECTOR AND METHOD OF INSTALLATION

(75) Inventor: Steven E. Wojcik, Shoreline, WA (US)

(73) Assignee: Aspire Bariatrics, Inc., Wilmington, DE (US)

( * ) Notice: Subject to any disclaimer, the term of this patent is extended or adjusted under 35 U.S.C. 154(b) by 603 days.

(21) Appl. No.: 14/239,916

(22) PCT Filed: Aug. 23, 2012

(86) PCT No.: PCT/US2012/051995
§ 371 (c)(1),
(2), (4) Date: Sep. 18, 2014

(87) PCT Pub. No.: WO2013/066480
PCT Pub. Date: May 10, 2013

(65) Prior Publication Data
US 2015/0038920 A1    Feb. 5, 2015

Related U.S. Application Data

(60) Provisional application No. 61/526,419, filed on Aug. 23, 2011.

(51) Int. Cl.
*A61J 15/00* (2006.01)
*A61M 39/28* (2006.01)
*A61M 25/02* (2006.01)

(52) U.S. Cl.
CPC ....... *A61J 15/0092* (2013.01); *A61J 15/0015* (2013.01); *A61J 15/0026* (2013.01); *A61J 15/0057* (2013.01); *A61M 39/28* (2013.01); *A61M 25/02* (2013.01); *A61M 2207/00* (2013.01); *Y10T 29/49947* (2015.01)

(58) Field of Classification Search
CPC ............... A61J 15/0092; A61J 15/0026; A61J 15/0015; A61J 15/0057; A61M 39/28; A61M 2207/00; A61M 25/02
See application file for complete search history.

(56) References Cited

U.S. PATENT DOCUMENTS

| | | | |
|---|---|---|---|
| 3,752,158 A | 8/1973 | Kariher | |
| 4,642,092 A | 2/1987 | Moss | |
| 4,668,225 A | 5/1987 | Russo | |
| 4,826,477 A * | 5/1989 | Adams | A61M 39/12 285/242 |
| 5,007,900 A * | 4/1991 | Picha | A61J 15/0015 604/106 |

(Continued)

FOREIGN PATENT DOCUMENTS

| | | |
|---|---|---|
| DE | 102 39 443 | 3/2004 |
| EP | 0059044 | 9/1982 |

(Continued)

OTHER PUBLICATIONS

European Patent Application No. 12845917: Supplementary Partial European Search Report dated Jun. 22, 2015, 11 pages.

(Continued)

*Primary Examiner* — Bradley Osinski
(74) *Attorney, Agent, or Firm* — Baker & Hostetler LLP

(57) ABSTRACT

Skin port connectors for use as part of a percutaneous gastrostomy tube assembly and methods for connecting such a device to such an assembly are disclosed.

27 Claims, 20 Drawing Sheets

(56) References Cited

U.S. PATENT DOCUMENTS

| | | |
|---|---|---|
| 5,417,664 A | 5/1995 | Felix |
| 5,716,347 A | 2/1998 | Gibbs et al. |
| 6,659,974 B1 | 12/2003 | Moss |
| 6,666,853 B2 | 12/2003 | Chu et al. |
| 6,979,322 B2 * | 12/2005 | Chu ............... A61J 15/0015 604/248 |
| 7,648,479 B2 | 1/2010 | Solovay et al. |
| 2003/0158539 A1 | 8/2003 | Bouphavichith et al. |
| 2003/0187424 A1 * | 10/2003 | Chu ............... A61J 15/0015 604/537 |
| 2003/0212385 A1 | 11/2003 | Brenner et al. |
| 2004/0193115 A1 | 9/2004 | Itrich et al. |
| 2006/0100604 A1 | 5/2006 | Brenner |
| 2006/0122559 A1 | 6/2006 | Shia |
| 2006/0135914 A1 | 6/2006 | Chu et al. |
| 2008/0033345 A1 | 2/2008 | Langloss et al. |
| 2008/0039809 A1 | 2/2008 | Kamen et al. |
| 2011/0082442 A1 | 4/2011 | Solovay et al. |
| 2011/0178480 A1 | 7/2011 | Solovay et al. |
| 2011/0190719 A1 | 8/2011 | Kamen et al. |

FOREIGN PATENT DOCUMENTS

| | | |
|---|---|---|
| EP | 2089094 A2 | 8/2009 |
| EP | 2089094 B1 | 8/2009 |
| JP | 2003-86233 | 3/2003 |
| JP | 2005-528135 | 9/2005 |
| WO | WO 02/32477 | 4/2002 |
| WO | WO 2006/020441 | 2/2006 |
| WO | WO2008054699 A2 | 5/2008 |
| WO | WO 2013/066480 | 5/2013 |

OTHER PUBLICATIONS

International Patent Application No. PCT/US2012/051995: International Search Report and Written Opinion dated Apr. 12, 2013, 22 pages.

Flegal et al, "Prevalence and Trends in Obesity Among US Adults", JAMA, Oct. 2002; 288,1723-1727.

International Patent Application No. PCT/US2007/017368: International Search Report and Written Opinion dated Mar. 7, 2008, 22 pages.

* cited by examiner

CUT END OF GASTROSTOMY TUBE

SKIN PORT CONNECTOR AND METHOD OF INSTALLATION

CROSS-REFERENCE TO RELATED APPLICATIONS

This application is the National Stage of International Application No. PCT/US2012/051995, filed Aug. 23, 2012, which claims the benefit of U.S. Provisional Application No. 61/526,419, filed Aug. 23, 2011, the disclosures of which are incorporated herein by reference in their entireties.

TECHNICAL FIELD

This invention relates to improved skin port connectors for use as part of a percutaneous gastrostomy tube assembly and methods for connecting such a device to such an assembly.

BACKGROUND

Obesity is a major health problem in the United States and other countries. The National Health and Nutrition Examination Survey (1988-1994) reported that approximately 20-25% of Americans are obese, while another study estimated the percentage of overweight Americans to be between 60% and 65% (Flegal K M, Carroll M D, Ogden C L, Johnson C L "Prevalence and trends in obesity among US adults, 1999-2000" JAMA 2002; 288:1723-1727). Obesity can cause numerous health problems, including diabetes, degenerative joint disease, hypertension, and heart disease. Weight reduction can be achieved by increased caloric expenditure through exercise and/or by reduced caloric consumption through diet. However, in most cases, weight gain often recurs and improvements in related co-morbidities are often not sustained.

Surgical procedures present an increasingly common solution for obese patients. Surgical procedures include, for example, stapled gastroplasty, banded gastroplasty, gastric banding, gastric bypass surgery, and bilopancreatic bypass. However, these surgical procedures are invasive, risky and expensive to perform, and many patients regain a substantial portion of the lost weight.

Gastrostomy is an alternative to these procedures for weight loss management. New methods of connecting the gastrostomy tubes originating in the stomachs of patients to ports which control the movement of material from the stomach to the outside world. The present invention describes embodiments directed to such skin ports.

SUMMARY

This invention relates to improved skin port connectors for use as part of a percutaneous gastrostomy tube assembly and methods for connecting such a device to such an assembly.

Certain embodiments provide skin port connectors for use on a flexible percutaneous gastrostomy tube, said tube having an inner mean cross-sectional dimension, an outer mean cross-sectional dimension, and a tube wall thickness when uncompressed, each skin port connector comprising:

(a) a skin flange containing a through-hole channel, said channel having (i) a main inner surface, (ii) a mean cross-sectional dimension and area, (iii) proximal and (iv) distal ends and (v) a center-line axis along the longitudinal axis of the channel, said channel further comprising (vi) a circumferential ridge protruding from the main inner surface into the channel of the through-hole at a position within the channel; the circumferential ridge defining a second mean cross-sectional dimension and area that are each less than the mean cross-section dimension and area of the main inner surface;

(b) a coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the sleeve body is located (viii) nearer the proximal end of the sleeve body than the distal end and defines (ix) a second mean outer cross-sectional dimension and area; and (c) an optional valve assembly adapted for attachment to said skin flange;

wherein at least a portion of the coupler fits within the through-hole channel so that the center-line axes of the through-hole channel and the coupler are substantially coaxial;

wherein the surface(s) of the circumferential ridge protruding from the main inner surface into the channel of the through-hole and the surface(s) of the circumferential ridge protruding from the sleeve body in closest approach to one another comprise mating surfaces with respect to one another;

wherein the second mean outer cross-sectional area defined by the circumferential ridge protruding from the sleeve body is less than the corresponding mean cross-section area defined by the main inner surface of the through-hole but more than the corresponding second mean cross-sectional area defined by the circumferential ridge of the through-hole; and wherein the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube to be used.

Other embodiments provide assemblies each comprising a skin port connector and a flexible percutaneous gastrostomy tube, said tube having an inner cross-sectional dimension, an outer cross-sectional dimension, and a tube wall thickness when uncompressed, said skin port connector comprising:

(a) a skin flange containing a through-hole channel, said channel having (i) a main inner surface, (ii) a mean cross-sectional dimension and area, (iii) proximal and (iv) distal ends and (v) a center-line axis along the longitudinal axis of the channel, said channel further comprising (vi) a circumferential ridge protruding from the main inner surface into the channel of the through-hole at a position within the channel; the circumferential ridge defining a second mean cross-sectional dimension and area that are each less than the mean cross-section dimension and area of the main inner surface;

(b) a coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the sleeve body is located (viii) nearer the proximal end of the sleeve body than the distal end and defines (ix) a second mean outer cross-sectional dimension and area; and (c) an optional valve assembly adapted for attachment to said skin flange;

wherein at least a portion of the coupler fits within the through-hole channel so that the center-line axes of the through-hole channel and the coupler are substantially coaxial;

wherein the surface(s) of the circumferential ridge protruding from the main inner surface into the channel of the through-hole and the surface(s) of the circumferential ridge protruding from the sleeve body in closest approach to one another comprise mating surfaces with respect to one another;

wherein the second mean outer cross-sectional area defined by the circumferential ridge protruding from the sleeve body is less than the corresponding mean cross-section area defined by the main inner surface of the through-hole but more than the corresponding second mean cross-sectional area defined by the circumferential ridge of the through-hole; and wherein the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube.

Still other embodiments provide apparatuses and methods for removing ingested food and/or liquid matter from a patient's stomach via a gastrostomy tube that passes through the patient's abdominal wall in the patient's stomach, wherein each apparatus (and method of using the same) comprises an assembly described herein and a pump for removing ingested food and/or liquid matter from a patient's stomach, said pump being in fluid communication with said assembly. In other embodiments, the apparatus comprises an assembly as described herein to which a second tubing in downstream fluid communication with the valve assembly is connected thereto, allowing for the passage drainage of the food and/or liquid matter from a patient's stomach.

Additional embodiments provide methods of connecting a skin port connector to a flexible percutaneous gastrostomy tube that passes from and through a patient's stomach, and exits through an external stoma on the patient's abdominal wall, said percutaneous gastrostomy tube having a distal end within the patient's stomach and a proximal end to be connected outside of the patient's body, wherein the proximal end of the tube, outside of the patient's body has an inner cross-sectional dimension, an outer cross-sectional dimension, and an uncompressed tube wall thickness, each method comprising:

(a) clamping the gastrostomy tube between the stoma and the end of the tube to be connected, so as to substantially prevent the flow of material out of the stomach;

(b) providing a clamp plate/tray having an area, through which the gastrostomy tube can pass;

(c) optionally trimming the proximal end of the gastrostomy tube at a pre-set distance from the stoma so as to provide an open proximal end;

(d) locating the optionally trimmed proximal end of the gastrostomy tube within a through-hole channel of a skin flange at a pre-determined height relative to through-hole; and (e) inserting a coupler into the open proximal end of the gastrostomy tube, said coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the sleeve body is located (viii) nearer the proximal end of the sleeve body than the distal end and defines (ix) a second mean outer cross-sectional dimension and area;

so that at least a portion of the coupler fits within the through-hole channel and the center-line axes of the through-hole channel and the coupler are substantially coaxial;

wherein the clamp plate/tray is capable of distributing any pressure associated with inserting the coupler over the area of the platform;

wherein the surface(s) of the circumferential ridge protruding from the main inner surface into the channel of the through-hole and the surface(s) of the circumferential ridge protruding from the sleeve body in closest approach to one another comprise mating surfaces with respect to one another;

wherein the second mean outer cross-sectional area defined by the circumferential ridge protruding from the sleeve body is less than the corresponding mean cross-section area defined by the main inner surface of the through-hole but more than the corresponding second mean cross-sectional area defined by the circumferential ridge of the through-hole; and wherein the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube;

so as to compress the tube radially between the through-hole and the coupler.

Other embodiments provide devices for connecting a skin port connector to a flexible percutaneous gastrostomy tube, each device comprising:

a clamp plate/tray having a base thickness less than about 10 mm, and comprising a tube opening, through which may pass the flexible percutaneous gastrostomy tube;

a movable clamp jaw attached to said clamp plate/tray and configured to be capable of clamping the flexible percutaneous gastrostomy tube which may pass through the clamp plate/tray; and optionally (a) at least one locator fixture capable of mating with the skin flange so as to hold the skin flange in a position fixed relative to the tube opening; and (b) at least one locator fixture capable of holding a tube cutting tool in a position fixed relative to the a position fixed relative to the tube opening.

Still other embodiments provide clamp plate/trays, each comprising features substantially as shown in FIG. 4; tube cutting tool assemblies, each comprising features substantially as shown in FIG. 6; sliding guide pin/mandrel combinations, each comprising features substantially as shown in FIG. 10; and couplers, each comprising features substantially as shown in FIG. 10.

Other embodiments provide kits, each kit comprising at least two of the following components: (a) a clamp plate/tray having a base thickness less than about 10 mm, and comprising a tube opening through which may pass the flexible percutaneous gastrostomy tube and optionally (i) at least one locator fixture capable of holding the skin flange in a position fixed relative to the tube opening; (ii) at least one locator fixture capable of holding a tube cutting tool in a position fixed relative to the a position fixed relative to the tube opening; and (iii) a movable clamp jaw attached to said clamp plate/tray and configured to be capable of clamping the flexible percutaneous gastrostomy tube which may pass through the clamp plate/tray; (b) a tube cutting tool assembly; (c) a sliding guide pin optionally attached to mandrel; and (d) a coupler comprising a sleeve body having a bore therethrough and a circumferential ridge and/or at least one other feature protruding from the outer surface of the sleeve body, said coupler having proximal and distal ends and a center-line axis along the longitudinal axis of the bore, said sleeve body having inner and outer surfaces and an inner mean cross-sectional dimension and area defined by the inner surface and a first outer mean cross-sectional dimension and area defined by the outer surface of the sleeve body, and wherein the circumferential ridge protruding from the sleeve body is located nearer the proximal end of the sleeve body than the distal end and defines a second mean outer cross-sectional dimension and area, wherein said guide pin has an external cross-sectional area substantially similar to that inner cross-sectional area of the coupler, such that the coupler is slidably detachable from the guide pin.

BRIEF DESCRIPTION OF THE DRAWINGS

The following drawings are illustrative embodiments of the invention but are not intended to limit the invention as encompassed by the claims forming part of the invention.

DETAILED DESCRIPTION OF ILLUSTRATIVE EMBODIMENTS

Figure 1:
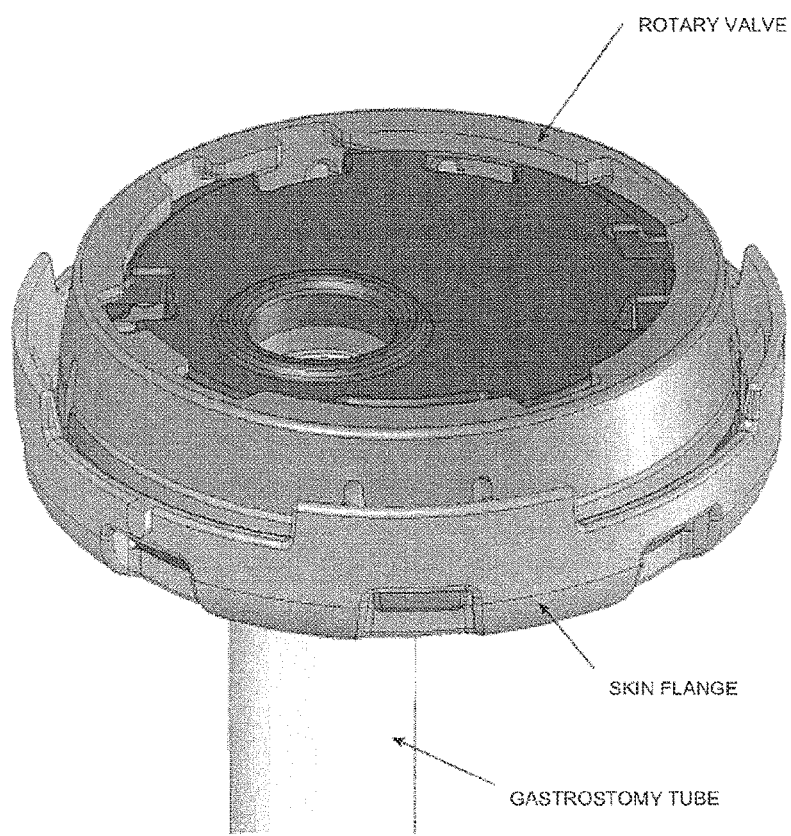
FIG. 1 illustrates one embodiment of a skin port attached to a gastrostomy tube.

The present invention relates generally to improved skin port connectors for use as part of a percutaneous gastrostomy tube assembly and methods for connecting such a skin port to such an assembly.

More specifically, the present invention(s) relates to a skin port connector with a valve mechanism coupled to the external end of a gastrostomy tube, which itself is in fluid communication with the stomach of a patient. The skin port is a critical part of the system since it seals the end of the gastrostomy tube to prevent the contents of the stomach from leaking until the valve is opened by the patient. Not only must the connection be strong, reliable, and well-sealed, but it should be low-profile to be unobtrusive under clothing, able to be re-connected to the gastrostomy tube as the tube length is shortened after weight loss, and easy to connect without trauma to the patient.

U.S. Pat. No. 7,648,479 and U.S. Patent Application Publication Ser. Nos. 2008/0039809, 2011/0082442, 2011/0178480, and 2011/0190719 describe systems and methods for removing ingested material from a stomach, each of which is incorporated by reference in its entirety for all its teaching. For example, Application Publication Ser. No. 2011/0082442 describes one possible method of achieving connecting a skin port connector with a valve mechanism coupled to the external end of a gastrostomy tube. It relies on an external helix on the exterior surface of the gastrostomy tube which connects to the skin port by screwing into the skin port. The present inventors have discovered that, in practice, use of this device can be problematic since the sealing area is not visible and it is possible to misalign the funnel portion of the valve with the end of the tube and damage the end of the tube creating a leak path.

An improved skin port and method of installation are described in this disclosure that eliminates the problems and disadvantages of the previous design. For example, the improved skin port allows the use of an elastomeric gastrostomy tube with a smooth constant cross-section, and makes for a more effective seal since the resilient tube material itself can be compressed.

The present invention may be understood more readily by reference to the following detailed description taken in connection with the accompanying Tables and Figures, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the method of preparing articles and to the resulting, corresponding physical articles themselves, as well as the referenced and readily apparent applications for such articles.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include each and every value within that range.

Where the term "optional" is used to describe a component or element, the invention includes separate embodiments where that component or element is present or absent.

It is to be appreciated that certain features of the invention which are, for clarity, described herein in the context of separate embodiments, may also be provided in combination in a single embodiment. For example, the present disclosure recites separate embodiments for skin port connector(s) (including kits), methods of installing, and methods of using said connectors. The invention provides at least for the combination of any given connector or assembly with any given method of use or method of connecting (or as appropriate, with any given device/tool or combination of devices/tools). However, for the sake of brevity, each possible combination and permutation of the recited embodiments is not recited. That is, this specification should be read as providing for each permutation of each embodiment, both within options within and between each given class of embodiments. Conversely, various features of the invention that are, for brevity, described in the context of a single embodiment, may also be provided separately or in any subcombination. Finally, while an embodiment may be described as part of a series of steps or part of a more general composition or structure, each said embodiment may also be considered an independent embodiment in itself.

As used herein, the terms "distal" and "proximal" refer to relative positions intended to be directed toward and away from a patient, respectively; i.e., from the perspective of a caregiver. For example, the distal end of a gastrostomy tube is the end of the tube inside the patient and the proximal end of a gastrostomy tube is that end extending away from the patient. Similarly, a distal end of a through-hole channel is that end of the channel closest to the patient when the device is in place (note that reference to "a position within the channel," in the context of the circumferential ridge, refers to a position between the distal and proximal ends; i.e., at a distance intermediate between the two ends) (see, e.g., FIG. 2). The distal end of a coupler is that end of the coupler intended to be inserted into the proximal end of the gastrostomy tube.

Figure 2:
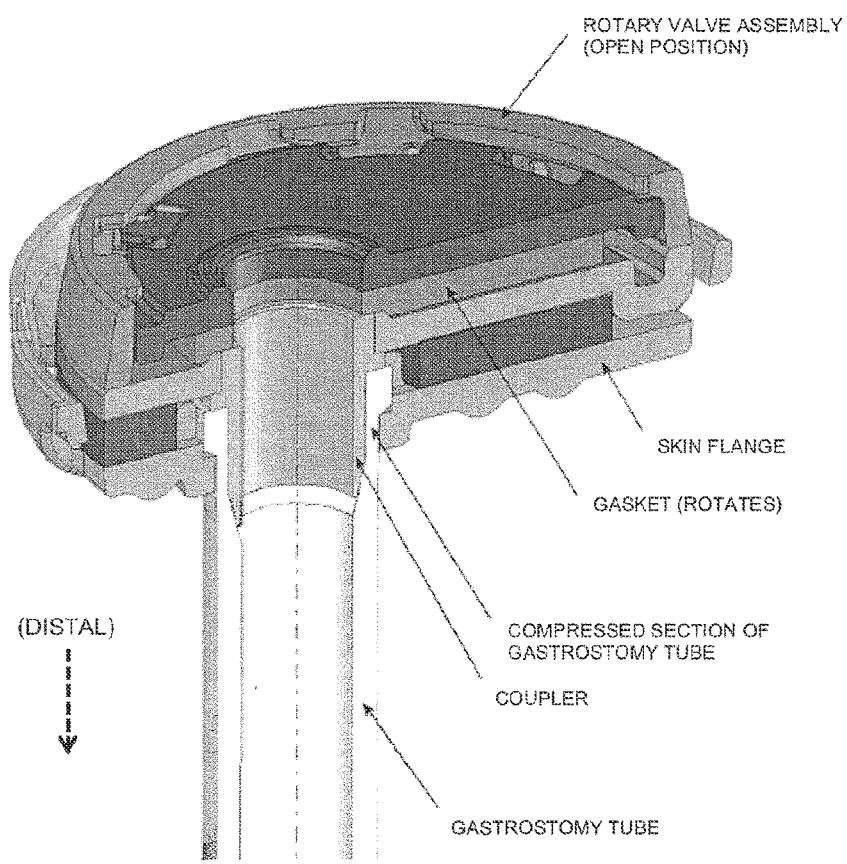
FIG. 2 illustrates a sectioned view of one embodiment of a skin port attached to a gastrostomy tube.

The improved skin port connector consists of a skin flange, a coupler, and an optional valve assembly (e.g., see FIGS. 1-2).

Various embodiments of the present invention provide skin port connectors for use on flexible percutaneous gastrostomy tubes, each tube having an inner mean cross-sectional dimension, an outer mean cross-sectional dimension, and a tube wall thickness when uncompressed, and each skin port connector comprising:

(a) a skin flange containing a through-hole channel, said channel having (i) a main inner surface, said channel having (ii) a mean cross-sectional dimension and area, (iii) proximal and (iv) distal ends and (v) a center-line axis along the longitudinal axis of the channel, said channel further comprising (vi) a circumferential ridge protruding from the main inner surface into the channel of the through-hole at a position within the channel; the circumferential ridge defining a second mean cross-sectional dimension and area that are each less than the mean cross-section dimension and area of the main inner surface;

(b) a coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the sleeve body is located (viii) nearer the proximal end of the sleeve body than the distal end and defines (ix) a second mean outer cross-sectional dimension and area; and (c) an optional valve assembly adapted for attachment to said skin flange;

wherein at least a portion of the coupler fits within the through-hole channel so that the center-line axes of the through-hole channel and the coupler are substantially coaxial;

wherein the surface(s) of the circumferential ridge protruding from the main inner surface into the channel of the through-hole and the surface(s) of the circumferential ridge protruding from the sleeve body in closest approach to one another comprise mating surfaces with respect to one another;

wherein the second mean outer cross-sectional area defined by the circumferential ridge protruding from the sleeve body is less than the corresponding mean cross-section area defined by the main inner surface of the through-hole but more than the corresponding second mean cross-sectional area defined by the circumferential ridge of the through-hole; and wherein the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube to be used.

Other embodiments provide assemblies comprising coupled skin port connectors and flexible percutaneous gastrostomy tubes, each tube having an inner cross-sectional dimension, an outer cross-sectional dimension, and a tube wall thickness when uncompressed, and each skin port connector comprising:

(a) a skin flange containing a through-hole channel, said channel having (i) a main inner surface, said channel having (ii) a mean cross-sectional dimension and area, (iii) proximal and (iv) distal ends and (v) a center-line axis along the longitudinal axis of the channel, said channel further comprising (vi) a circumferential ridge protruding from the main inner surface into the channel of the through-hole at a position within the channel; the circumferential ridge defining a second mean cross-sectional dimension and area that are each less than the mean cross-section dimension and area of the main inner surface;

(b) a coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the sleeve body is located (viii) nearer the proximal end of the sleeve body than the distal end and defines (ix) a second mean outer cross-sectional dimension and area; and (c) an optional valve assembly adapted for attachment to said skin flange;

wherein at least a portion of the coupler fits within the through-hole channel so that the center-line axes of the through-hole channel and the coupler are substantially coaxial;

wherein the surface(s) of the circumferential ridge protruding from the main inner surface into the channel of the through-hole and the surface(s) of the circumferential ridge protruding from the sleeve body in closest approach to one another comprise mating surfaces with respect to one another;

wherein the second mean outer cross-sectional area defined by the circumferential ridge protruding from the sleeve body is less than the corresponding mean cross-section area defined by the main inner surface of the through-hole but more than the corresponding second mean cross-sectional area defined by the circumferential ridge of the through-hole; and wherein the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube, such that the tube is compressed radially between the through-hole and the coupler.

The cross-sections of the through-hole, tube, and solid sleeve body may be any shape (e.g., including oval or polygonal, e.g., square, pentagonal, hexagonal, heptagonal, octagonal, or higher), though they are preferably matched in shape (i.e., the cross-sectional shapes of the elements are substantially the same (e.g., all circular or the same polygonal shape). In preferred embodiments, these cross-sectional shapes are substantially circular or round. For non-round cross-sections, the term "mean cross-sectional dimension" refers to an effective diameter corresponding to a constructed circle having the same area as the shape of the actual cross-section. The term "mean cross-sectional area" refers to the area of the constructed circle defined by that effective diameter. In those embodiments wherein the through-hole, tube, and solid sleeve body are all shaped as cylinders having circular cross-sections, the mean cross-sectional dimension is the diameter of the corresponding circular cross-sections and the areas are those areas defined by these diameters.

As used herein, the term "center-line axis along the longitudinal axis" of each described element or component refers to the imaginary line which passes along the length of the element, said line defined by points approximately corresponding to the center points of the constructed circles along the length of the element.

While the centerline axis of each of the elements should at least be parallel to one another in use, they are preferably "substantially coaxial" (reflecting real differences owing to manufacturing) such that the elements can stack within one another as otherwise described.

In various embodiments, the circumferential ridge of the coupler may be continuous or discontinuous and/or may also comprise other features providing the same function as the ridge; e.g., protruding nodes, pins, or other similar features. In other embodiments, the circumferential ridge protruding from the main inner surface into the channel of the through-hole may also be described as a shelf, and/or may comprise similar features as described above for the circumferential ridge of the coupler.

As described through-out, unless otherwise stated or apparent, references to various embodiments refer both to the skin port connectors, or parts thereof containing the skin flange, and assemblies containing the skin port connector or parts thereof.

As described herein, in various embodiments, the flexible percutaneous gastrostomy tube of the connector or the assembly comprises an elastomeric polymer. Preferred materials include polymers comprising silicone and/or polyurethane or mixtures or copolymers thereof. In preferred embodiments, these materials are durable and medical grade (e.g., bioinert, tissue-friendly) and most preferably suitable for use in human patients (i.e., is approved for use by appropriate regulatory agencies, e.g., the Food and Drug Agency in the United States).

In certain embodiments, the flexible percutaneous gastrostomy has a substantially smooth constant inner mean cross-sectional dimension. The inner and outer surfaces of the tube may be substantially smooth. Further embodiments provide that the wall thickness of the uncompressed percutaneous gastrostomy tube is in the range of about 0.5 mm to about 5 mm, preferably in the range of about 1 mm to about 4 mm, in the range of about 1 mm to about 3 mm, or in the range of about 1 mm to about 2 mm.

In some embodiments, the length of the through-hole channel of the connector or the assembly has a length in the range of about 2 mm to about 20 mm, preferably in the ranges of about 4 mm to about 20 mm, about 4 mm to about 10 mm, or about 4 mm to about 8 mm.

The invention also provides embodiments wherein the coupler or the sleeve body of the coupler has a length in the range of about 4 mm to about 20 mm, preferably in the ranges of about 4 mm to about 20 mm, about 4 mm to about 10 mm, or about 4 mm to about 8 mm. Relative to the length of the through-hole, the coupler or sleeve body may be either longer or shorter, preferably longer.

In various embodiments, the main inner surface of the through-hole channel is cylindrical, preferably having a smooth surface. The channel may have a constant diameter along the length of the channel, or may be tapered. If tapered, the distal end of the taper preferably has a smaller diameter/cross-section than the proximal end.

In describing various embodiments of the present invention, it is convenient to describe the through-hole channel and the coupler (and/or sleeve body thereof) in context with one another. However, it should be appreciated that each of these are independent components or elements.

Accordingly, in various embodiments of the coupler, the outer surface of the sleeve body is cylindrical (independent of the shape of the through-hole channel), preferably having a smooth surface. The sleeve body may have a constant diameter along its length of the channel, or may be tapered. If tapered, the distal end of the taper preferably has a smaller diameter/cross-section than the proximal end. While it may be preferred that any taper associated with the channel and/or the sleeve body be matched, it is not necessary that they do match.

It should be appreciated that, in use, the circumferential ridge protruding from the sleeve body sleeve is intended to be used in concert with the circumferential ridge of the through-hole. One purpose of these mating surfaces is to prevent the coupler from passing through the through-hole, when pushed or pulled to do so. The surface is also at least responsible for ensuring the integrity of the connection of the gastrostomy tube to the skin port connector and providing a seal which prevents fluid from leaking from the device when in use. Accordingly, in certain embodiments, mating surface of the circumferential ridge protruding from the sleeve body sleeve is complementary to the shape(s) of the circumferential ridge of the through-hole. That is, when placed together as described and shown, the surfaces of the two elements provide essential or substantially mated pairs of surfaces, whether flat—e.g. orthogonal or otherwise relative to the outer surface of the sleeve body/main inner surface of the through-hole, or whether nodule or slot protrusions from one element fits within grooves of the other element. In some embodiments, the mating surface of the circumferential ridge protruding from the sleeve body and the circumferential ridge of the through-hole are orthogonal to the sleeve body and the main inner surface of through-hole body, respectively. In other embodiments, the mating surfaces are non-orthogonal to their respective components. In sill other embodiments, the mating surfaces may be undulating, so as to increase the actual contact length between the two. Also, while some embodiments are described as circumferential (i.e., closed loop around elements), in other embodiments, these mated surfaces may be matching threads.

Further embodiments provide that the difference between the second mean cross-sectional dimension provided by the circumferential ridge of the through-hole and the mean cross-section dimension of the main inner surface is in the range of about 2 mm to about 10 mm, preferably in the range of about 2 mm to about 8 mm or in the range of about 2 mm to about 6 mm (i.e., the ridge extends a distance in the range of about 1 mm to about 5 mm into the channel of the through-hole, preferably in the range of about 1 mm to about 4 mm or in the range of about 1 mm to about 3 mm). In an analogous fashion, the difference between the first outer mean cross-sectional dimension corresponding to the outer surface of the body of the sleeve and the second mean outer cross-sectional dimension provided by the circumferential ridge protruding from the body is in the range of about 2 mm to about 10 mm, preferably in the range of about 2 mm to about 8 mm or in the range of about 2 mm to about 6 mm (i.e., the circumferential ridge and/or at least one other feature protrudes about 1 mm to about 5 mm from the outer surface of the body of the sleeve; preferably in the range of about 1 mm to about 4 mm or in the range of about 1 mm to about 3 mm). When in use, the overlap between these two ridges may be in the range of about 0.5, 1, 1.5, or 2 mm.

In certain embodiments, the circumferential ridge or other feature protruding from the sleeve body is located nearer the proximal end of the sleeve body than the distal end of the sleeve body. In preferred embodiments, this ridge or other feature is located within a distance in the range of about 0.5 mm to about 3 mm of the proximal end of the sleeve body, preferably in a range of about 0.5 mm to about 1.5 mm, or about 1 mm. In other embodiments, this ridge or other protruding feature is located within the first 25% of the distance between the proximal and distal ends of the sleeve body.

The distal end of the sleeve body may be chamfered, to help guide the sleeve body into the end of the gastrostomy tube during installation. See, e.g., FIG. 10. The coupler may comprise polymer or metal, preferably polymer, provided the material is capable of maintaining its structural integrity under the demands of the application and comprise such a material as resistant to corrosion, pitting, or other destruction which might result from contacting the content of the patient's stomach. Acid resistant thermoplastic materials, including ABS polymer, are suitable materials.

The inner surface of the sleeve body of the coupler may be rough, contain internal features (e.g., rifling), be substantially smooth, or polished, wherein the term "substantially smooth" refers to a surface to which no features deliberately added during the manufacturing of the coupler. The coupler is preferably not rough, so as to provide minimal wall friction to the free flow of materials therethrough while in use. Similarly, in certain preferred embodiments, the inner mean cross-sectional dimension of the sleeve body is substantially similar to or even greater than the inner mean cross-sectional dimension of the uncompressed percutaneous gastrostomy tube. This provides for the free-flow of material through the coupler and the connector when in use. This requires that the end of the gastrostomy tube stretch over the end of the coupler as the coupler is inserted into the tube. Therefore, the tubing must be clamped between the surface of the skin and the bottom of the skin flange to install the sleeve body.

Figure 20:
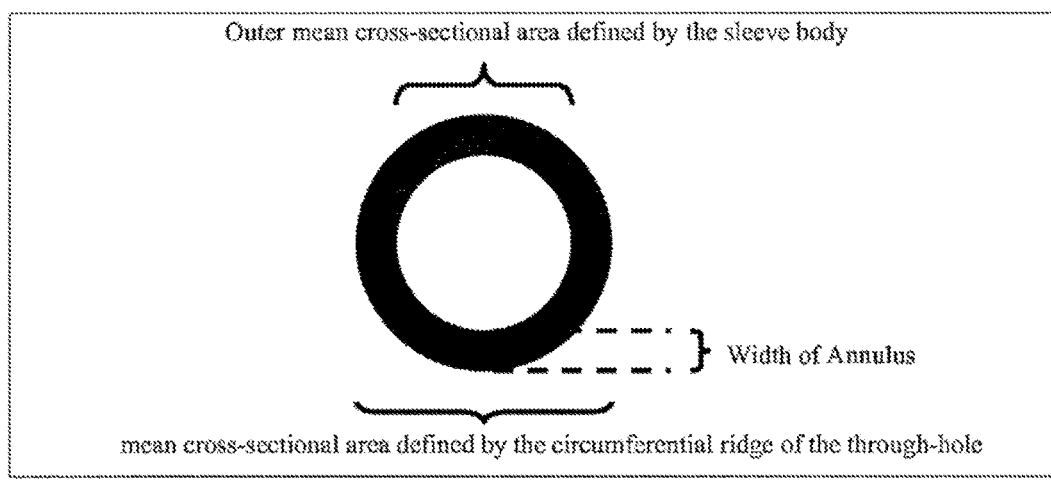
FIG. 20 illustrates a relationship between the mean cross-sectional area defined by the circumferential ridge of the through-hole, the outer mean cross-sectional area defined by the sleeve body, and the annulus.

In various embodiments, the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube to be used in a skin port connector or used in an assembly (see, e.g., FIG. 20). In independent embodiments, the width of the annulus is in the range of about 5% to about 90%, about 10% to about 80%, about 20% to about 60%, about 30% to about 50% of the thickness of the tube wall of the uncompressed percutaneous gastrostomy tube to be used in a skin port connector or used in an assembly. In certain embodiments the width of this annulus is substantially constant around its circumference.

As described herein, the end of gastrostomy tube is compressed radially between the through-hole channel of the skin flange and the outer surface of the body sleeve of the coupler. The radial compression on the wall of the tubing is determined by the clearance between the through-hole and the outer diameter(s) of the coupler/sleeve. The compression on the gastrostomy tube wall may be in a range of 5 to 90% depending on the specific durometer and material used for the gastrostomy tube and the desired axial holding strength of the joint. However, higher compression requires greater axial force to insert the sleeve body.

The proximal end of the coupler is intended to fit into a hole in the bottom of the valve assembly and so as to be covered by a sliding seal in the valve assembly when the valve is in the closed position. The valve assembly may be similar to the rotary valve described in U.S. Patent Application Publication Ser. Nos. 2008/0039809 and 2011/0190719, each of which is incorporated by reference herein at least for this purpose, or other valve mechanism as long as the seal covers the proximal end in the closed position and uncovers the proximal end to allow flow in the open position.

Various embodiments of the connector or the assembly further comprise a valve assembly. The valve assembly may include an actuator (e.g., slide, rotary, toggle, push-button, etc.) that permits the user to open or close the fluid path of the tube, as desired. The valve prevents and allows fluid flow into and out of the tube during use. One preferred embodiment is describe in U.S. Patent Application Ser. Nos. 2008/0039809, which is incorporated by reference in its entirety. Such an embodiment may comprise (a) a first platform and having a first thru-hole that passes therethrough, wherein the first platform is adapted for placement adjacent to a patient's skin; (b) a second platform having a second thru-hole that passes therethrough; and (c) a retainer configured to retain the first platform in proximity to the second platform such that the second platform can be rotated with respect to the first platform between a first position and a second position, wherein in the first position the first and second thru-holes align to provide access to the fluid pathway and in the second position the first and second thru-holes offset to provide a fluid tight seal and to prevent access to the fluid pathway.

In addition to skin port connectors for use on flexible percutaneous gastrostomy tubes or assemblies comprising coupled skin port connectors and flexible percutaneous gastrostomy tubes, the present invention also encompasses those apparatuses (and methods using the same) for removing ingested food and/or liquid matter from a patient's stomach via a gastrostomy tube that passes through the patient's abdominal wall in the patient's stomach, each apparatus comprising one of the described assemblies and a pump for removing ingested food and/or liquid matter from a patient's stomach, said pump being in fluid communication with said assembly. In other embodiments, the apparatus comprises an assembly as described herein to which a second tubing in downstream fluid communication with the valve assembly is connected thereto, allowing for the passage drainage of the food and/or liquid matter from a patient's stomach. Further features of such systems and methods are generally described in U.S. Pat. No. 7,648,479 and U.S. Patent Application Ser. Nos. 2008/0039809, 2011/0082442, 2011/0178480, and 2011/0190719, each of which is incorporated by reference in its entirety for all teachings contained therein.

Still other embodiments of the present invention include methods of connecting a skin port connector to a flexible percutaneous gastrostomy tube and devices for use in such methods. Again, for sake of clarity, these may be described in context of one another. However, each of the methods (and steps thereof) and the devices (and parts thereof) represent individual embodiments, which do not necessarily depend on one another. Nothing described herein should be construed as necessarily requiring a particular device for a particular method, or vice versa.

Accordingly, embodiments provide methods of connecting a skin port connector to a flexible percutaneous gastrostomy tube that passes from and through a patient's stomach, and exits through an external stoma on the patient's abdominal wall, said percutaneous gastrostomy tube having a distal end within the patient's stomach and a proximal end to be connected outside of the patient's body, wherein the proximal end of the tube, outside of the patient's body has an inner cross-sectional dimension, an outer cross-sectional dimension, and an uncompressed tube wall thickness, wherein each method comprises:

(a) clamping the gastrostomy tube between the stoma and the end of the tube to be connected, so as to substantially prevent the flow of material out of the stomach;

(b) providing a clamp plate/tray having an area, through which the gastrostomy tube can pass;

(c) optionally trimming the proximal end of the gastrostomy tube at a pre-set distance from the stoma so as to provide an open proximal end;

(d) locating the optionally trimmed proximal end of the gastrostomy tube within a through-hole channel of a skin flange at a pre-determined height relative to through-hole; and (e) inserting a coupler into the open proximal end of the gastrostomy tube, said coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the sleeve body is located (viii) nearer the proximal end of the sleeve body than the distal end and defines (ix) a second mean outer cross-sectional dimension and area;

so that at least a portion of the coupler fits within the through-hole channel and the center-line axes of the through-hole channel and the coupler are substantially coaxial;

wherein the clamp plate/tray is capable of distributing any pressure associated with inserting the coupler over the area of the platform;

wherein the surface(s) of the circumferential ridge protruding from the main inner surface into the channel of the through-hole and the surface(s) of the circumferential ridge protruding from the sleeve body in closest approach to one another comprise mating surfaces with respect to one another;

wherein the second mean outer cross-sectional area defined by the circumferential ridge protruding from the sleeve body is less than the corresponding mean cross-section area defined by the main inner surface of the through-hole but more than the corresponding second mean cross-sectional area defined by the circumferential ridge of the through-hole; and wherein the difference between the second mean cross-sectional area defined by the circumferential ridge of the through-hole and the outer mean cross-sectional area defined by the sleeve body defines an annulus, said annulus having a width that is less than the thickness of the tube wall of the uncompressed percutaneous gastrostomy tube;

so as to compress the tube radially between the through-hole and the coupler.

These methods may further comprise attaching a valve assembly to the skin flange, such that the valve assembly seals the proximal end of the tube, thereby preventing prevent the flow of material out of the stomach on release of the clamping. These methods may also comprise removing the clamp from the tube after the tube is connected to the skin port connector (i.e., unclamping the gastrostomy tube).

Clamping the tubing eliminates the need to plug the gastrostomy tube while the skin port is connected to prevent leakage. Since it is desirable to keep the gap between the skin and bottom of the skin flange as small as possible to hide the skin port under clothing, the clamping mechanism should also be relatively thin. While a pair of locking forceps or similar instrument may be used as a clamp, using a small clamping plate (FIG. 3) or tray has the advantage of providing a stable place to rest the skin flange while the coupler is inserted. Also, the force transmitted to the patient can be minimized by gripping the plate while pressing the coupler in place. The clamping mechanism on the clamp plate could be a simple slot that is slightly less than twice the wall thickness of the gastrostomy tube in which the tubing is forced into or a clamp with at least one movable jaws. An example of such a clamp is shown in FIG. 4 which one jaw of the clamp is part of the clamping plate and the movable jaw hinges on one end and is latched on the other end. A variety of different clamp designs know in the art could be used as long as they are relatively low-profile in the area around the clamped tubing.

Figure 3:
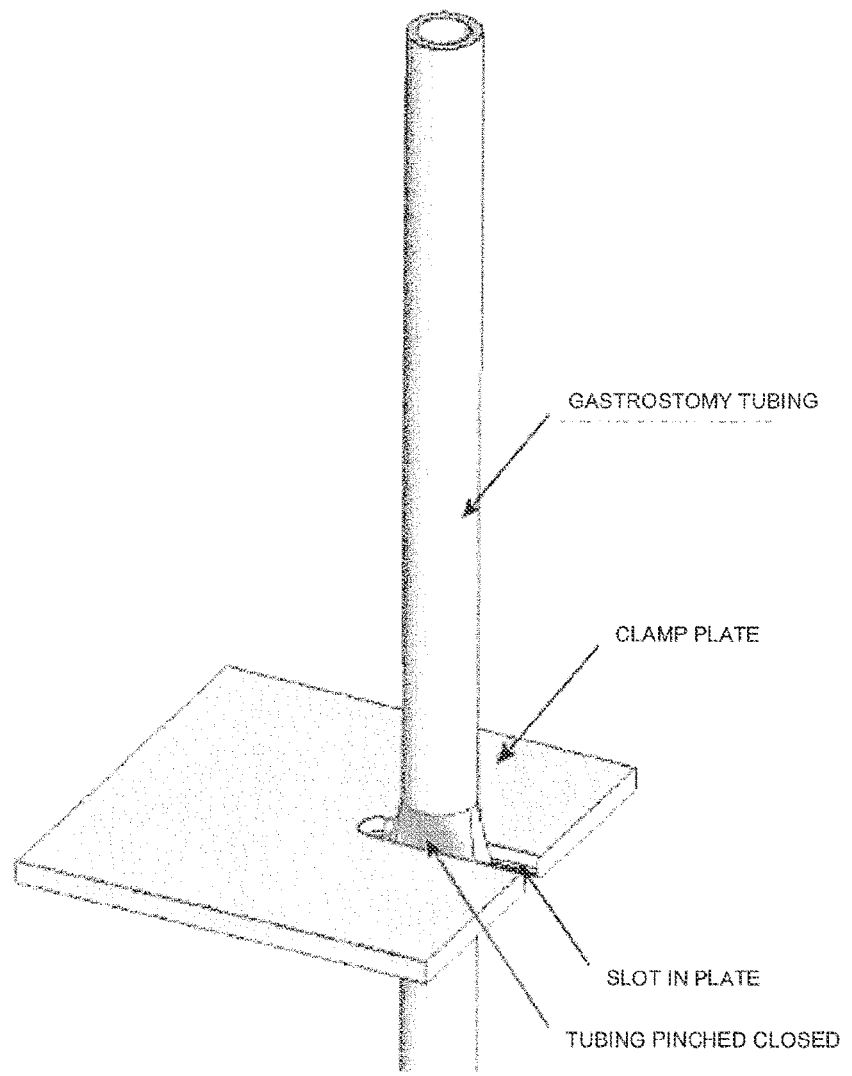
FIG. 3 illustrates one embodied concept of clamping a gastrostomy tube.
Figure 4:
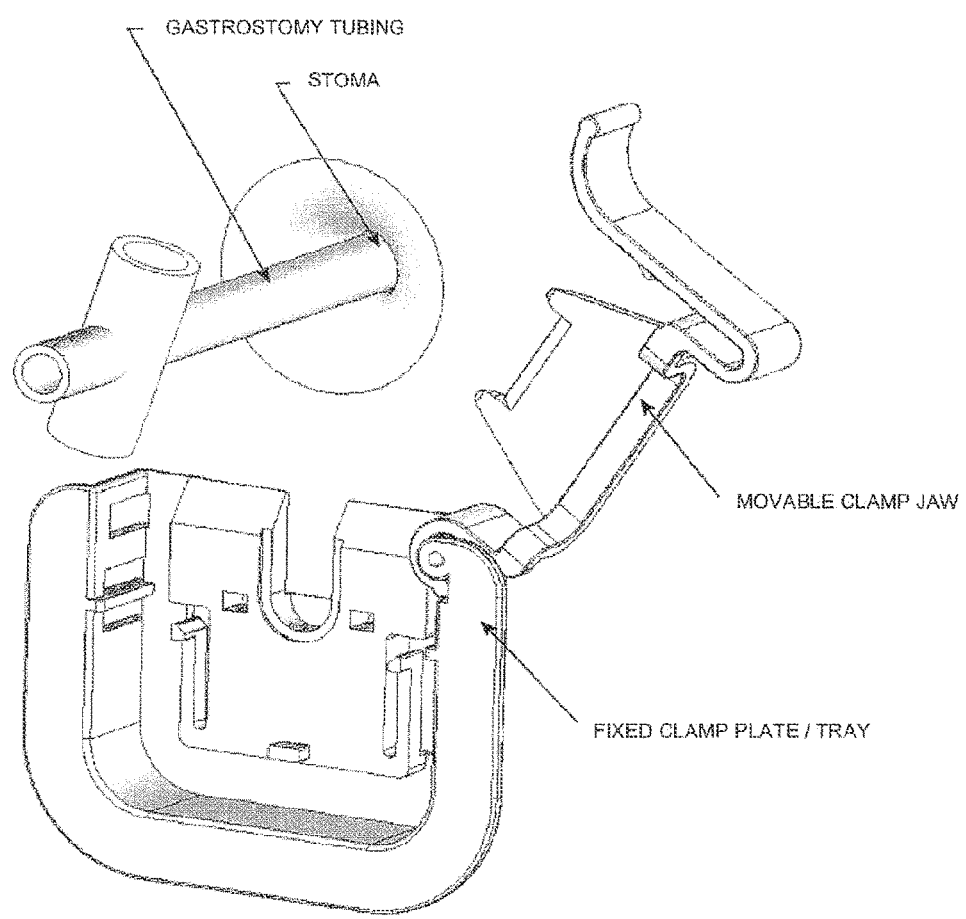
FIG. 4 illustrates one embodiment of a installing clamp tray, showing one embodied movable clamp jaw, and providing an illustration of its use relative to a gastrostomy tube emerging from the stoma of a patient.
Figure 5:
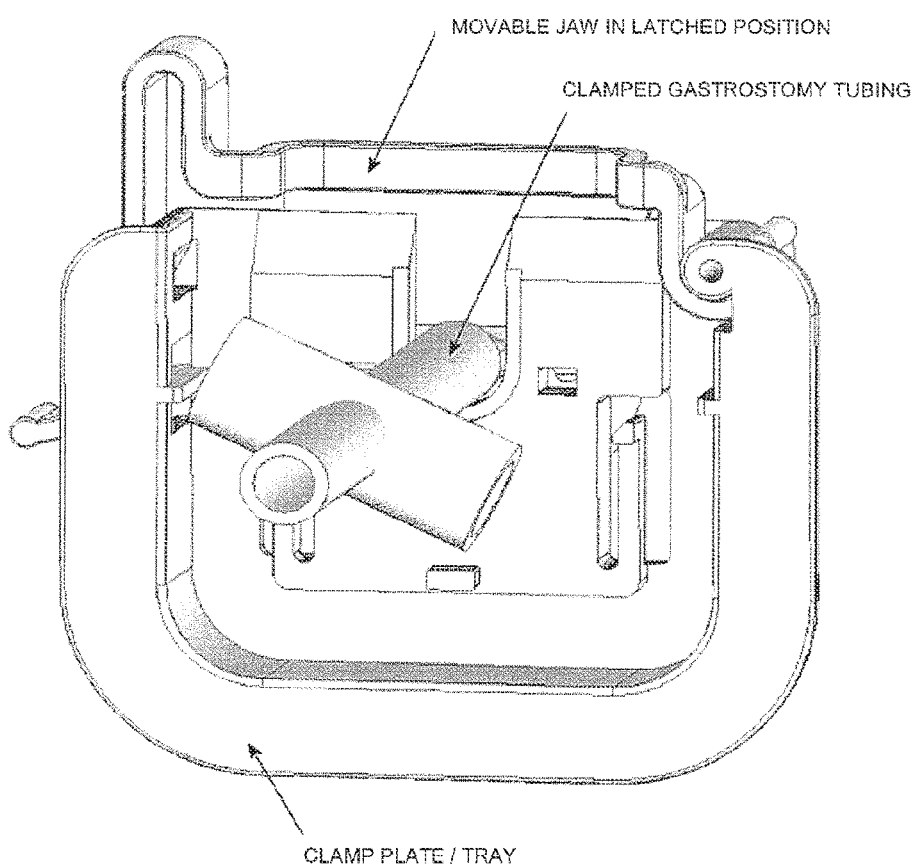
FIG. 5 illustrates one embodiment of a installing clamp tray, wherein the movable clamp jaw of FIG. 4 is closed, thereby holding the gastrostomy tube in place.

One embodiment of the general concept of clamping the gastrostomy tube between the stoma and the end of the tube to be connected, so as to substantially prevent the flow of material out of the stomach is shown in FIG. 3. Other embodiments provide that the clamping comprises collapsing the tube using a movable clamp jaw pincer, hinged or otherwise affixed to a clamp plate/tray, or by use of a free-standing or detachable clamp. One non-limiting embodiment of such a movable clamp jaw pincer is illustrated in FIGS. 4-5. In preferred embodiments, a movable clamp jaw pincer is connected to a frame capable of attaching and/or holding a tube cutting tool and/or the skin flange in a substantially fixed and pre-specified position relative to the frame.

Figure 9:
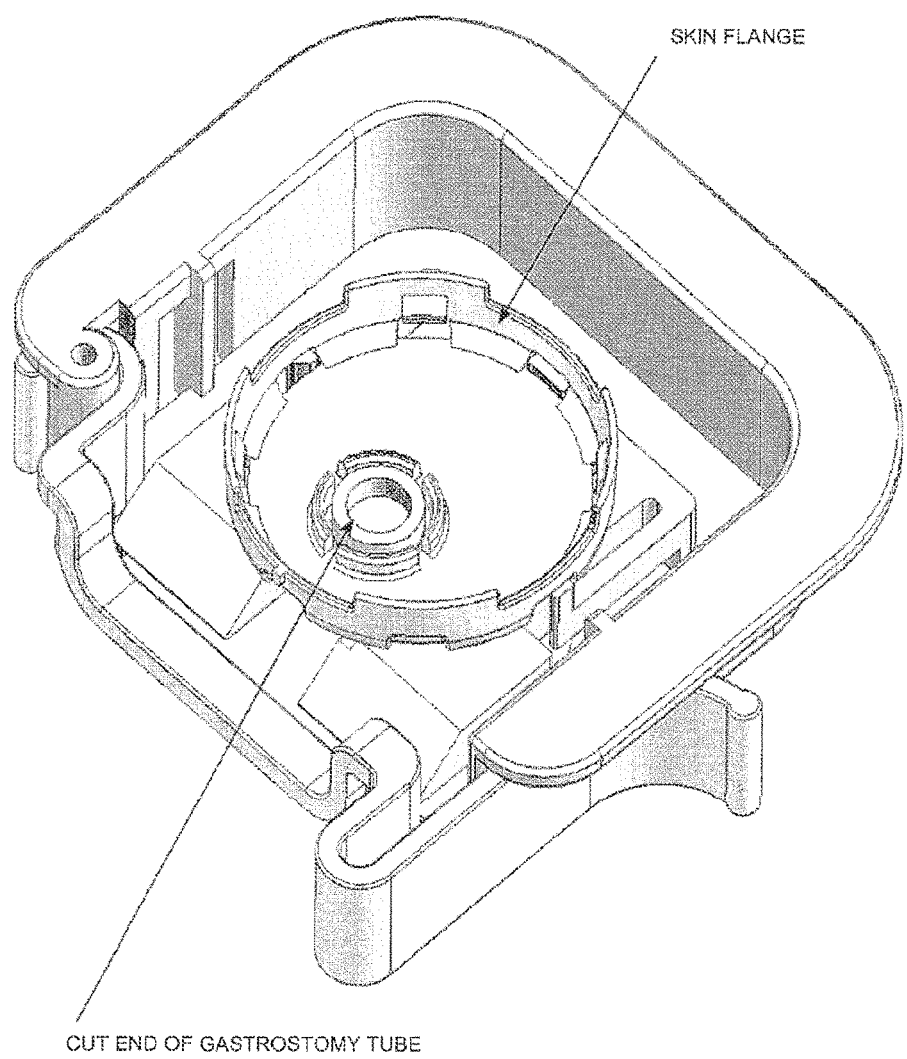
FIG. 9 illustrates one embodiment of the skin flange having been mounted over the clamped tube cut to length as held by the installing clamp tray of FIG. 8.

Once the gastrostomy tube is clamped, other embodiments provide that the proximal end of the tube be positioned through the through-hole channel of a skin flange, for example as shown in FIG. 9, preferably positioned so that the open proximal end of the tube extends above the proximal end of the channel.

In some embodiments, the proximal end of the gastrostomy tube is trimmed, either to shorten the tube or provide a clean surface for contacting the later applied valve plate, or both. This trimming can be done either before or after positioning the tube with respect to the through-hole channel of the skin flange. The trimming may effected by a scalpel, scissors, or preferably a specific device configured with a blade oriented perpendicular to the tube. One non-limiting embodiment of this is shown in FIGS. 6-9, wherein the trimming is shown to be done before positioning the tube with respect to the through-hole channel. Other cutting instruments/configurations may also be employed.

Figure 14:
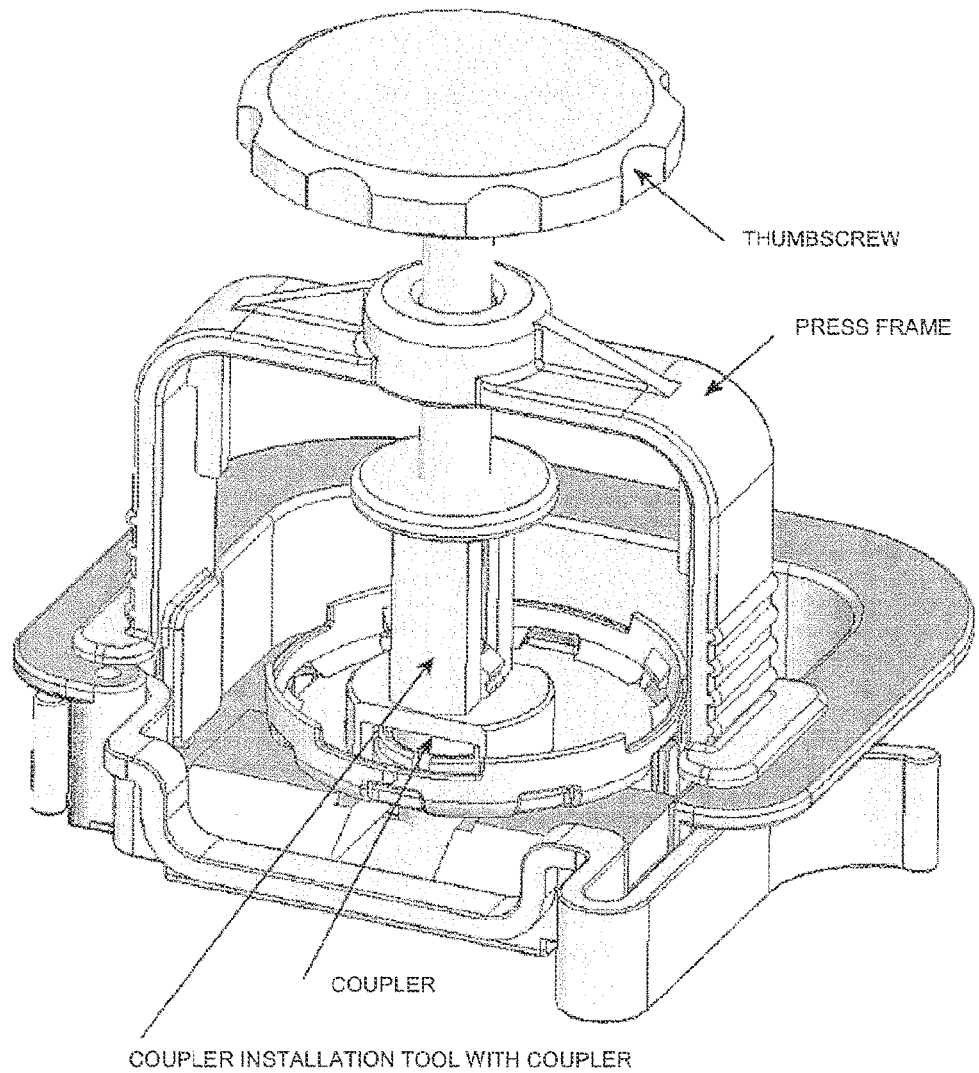
FIG. 14 illustrates an alternative embodiment of installing the coupler into the tube, in which a press frame with thumbscrew is employed.

Once the tube is properly positioned with respect to the through-hole channel, the coupler may be press fit or screwed (depending on its configuration) into the open proximal end of the tube to compress and seal the tubing, as well as secure the tubing to the skin flange. A clamp frame which attaches to the clamp plate with a thumbscrew which presses the coupler into the tubing as the thumbscrew is rotated may also be used, particularly if the compression of the tubing is relatively high (e.g., FIG. 14). Whether press fit or screwed into the open proximal end of the tube, it is inserted to a distance defined by further inability of the circumferential ridge protruding from the sleeve body surface(s) to pass beyond the circumferential ridge protruding from the main inner surface into the channel of the through-hole in the presence of the compressed tube.

Figure 10:
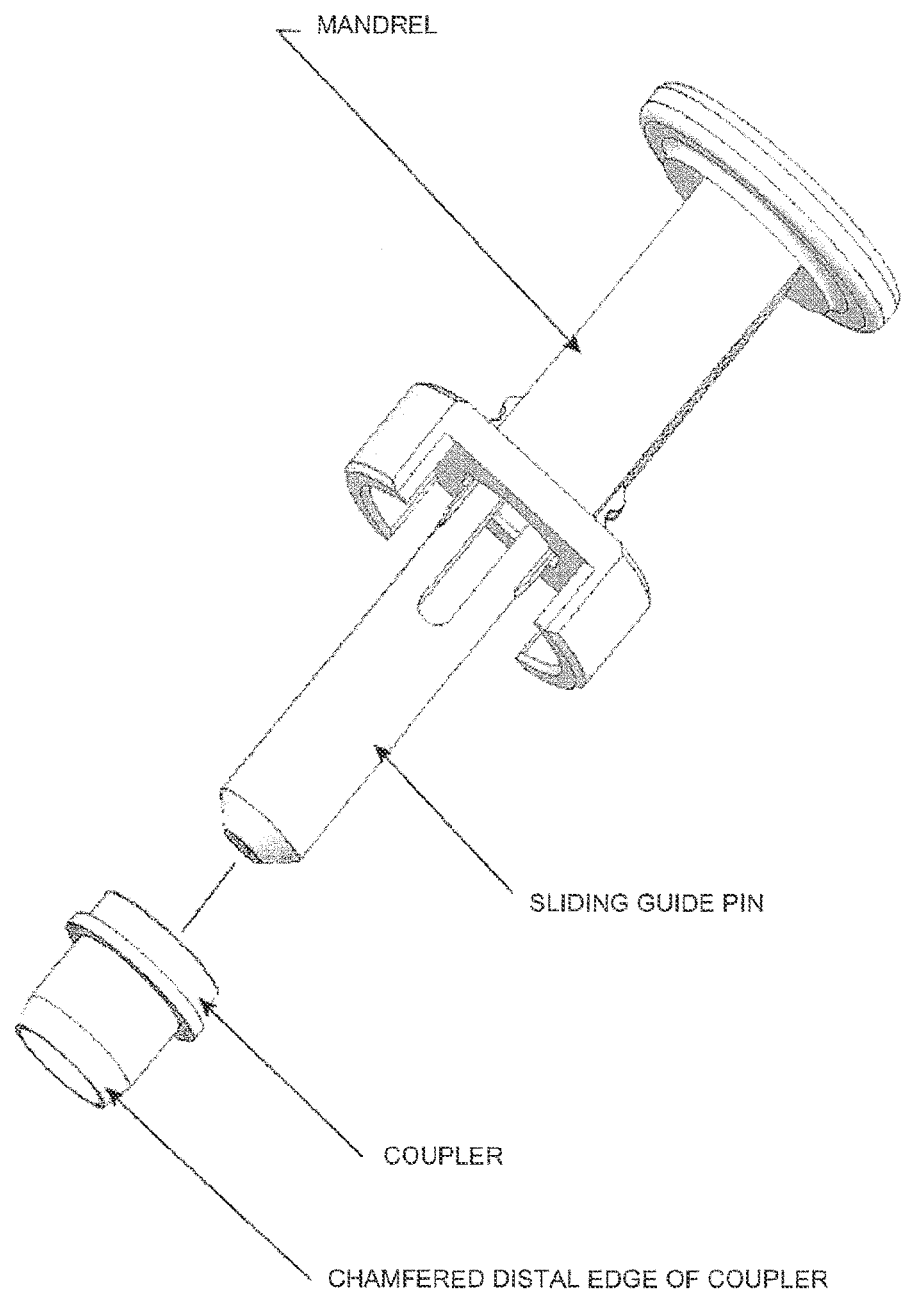
FIG. 10 illustrates one embodiment of the sliding guide pin/mandrel assembly as described herein and one embodied coupler of the present invention.
Figure 11:
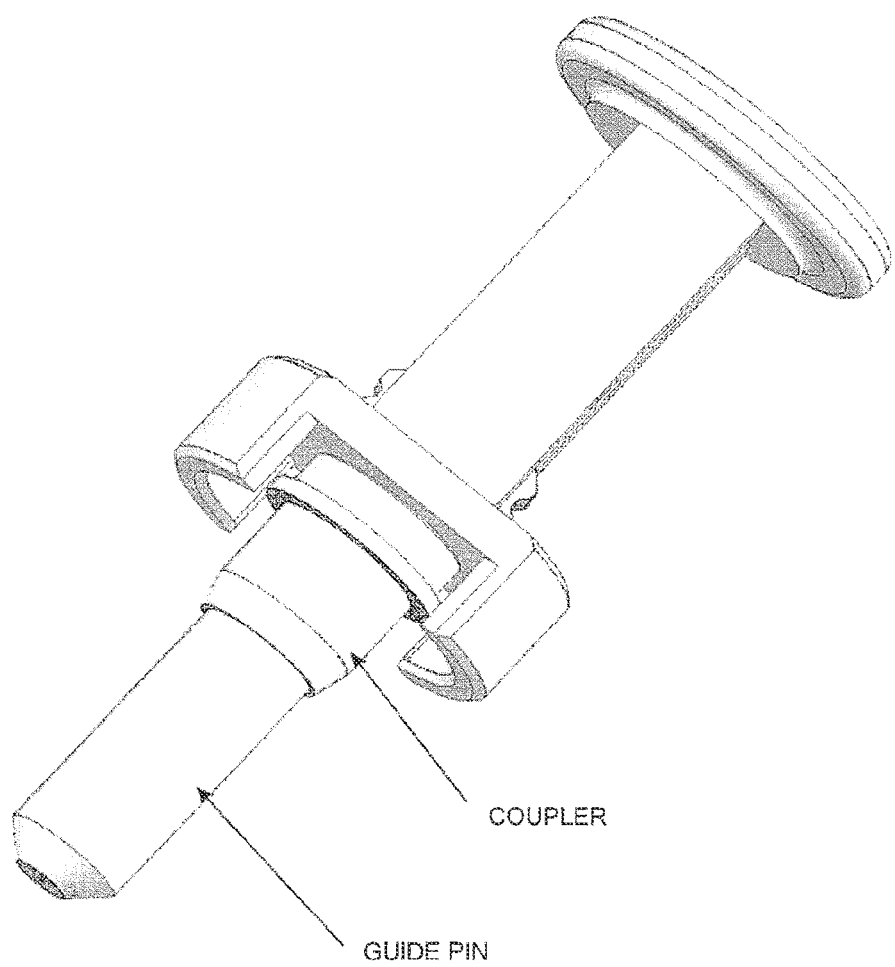
FIG. 11 illustrates one embodied coupler positioned on one embodied sliding guide pin/mandrel assembly as described herein.

The insertion of the coupler may be accomplished by hand, with or without the use of tools or devices. A drop of water or saline solution on the end of the tubing may also be used as a lubricant to aid the installation of the coupler but is not required. However, in certain embodiments, the coupler is guided into the open proximal end of the gastrostomy tube using a guide pin, said guide pin having an external cross-sectional area substantially similar to that inner cross-sectional area of the coupler, said coupler being slidably detachable from the guide pin. One non-limiting embodiment of this guide pin is illustrated in FIGS. 10-11. In these figures, the guide pin is shown attached to a mandrel. While preferred, this configuration is not required, and other embodiments provide for the use of a guide pin free of such a mandrel.

Figure 12:
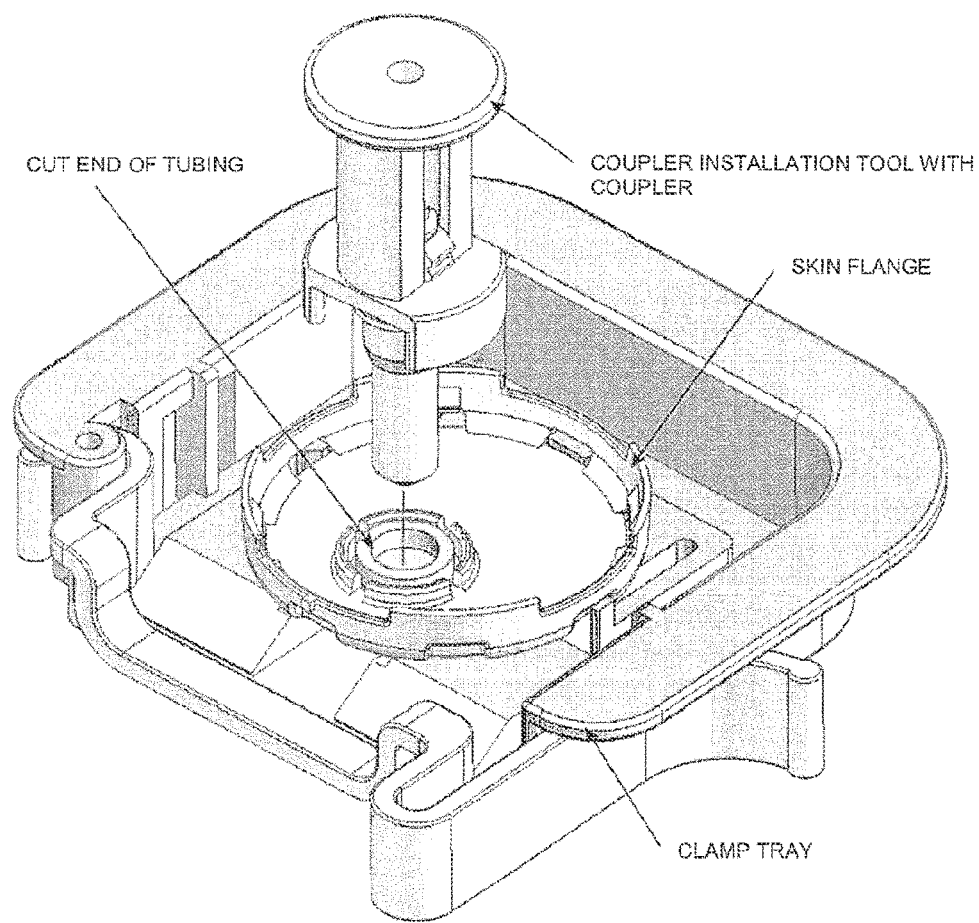
FIG. 12 illustrates a positioning of the coupler/sliding guide pin/mandrel assembly relative to the open proximal end of a cut gastrostomy tube before insertion of the sleeve body into the tube.
Figure 13:
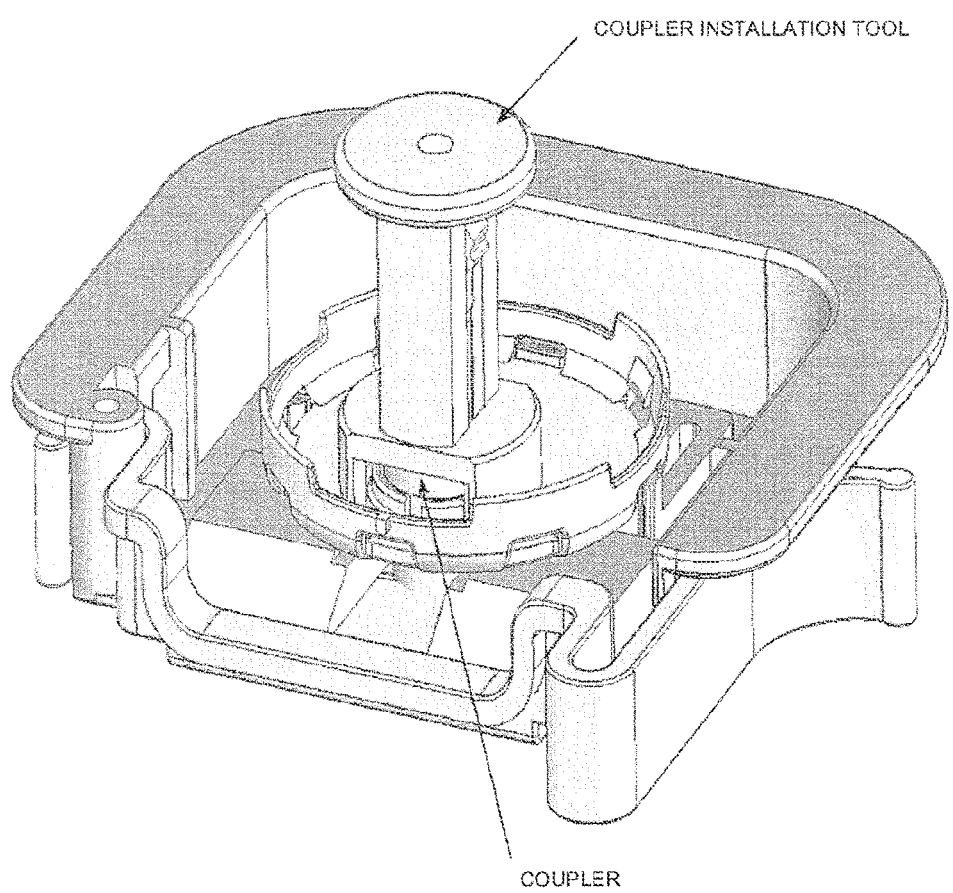
FIG. 13 illustrates a positioning of the coupler/sliding guide pin/mandrel assembly relative to the open proximal end of a cut gastrostomy tube after insertion of the coupler into the tube.

The purpose of the guide pin is to help hold the coupler while inserting it into the open end of the tube. Accordingly, the inner cross-sectional dimension of the sleeve body of the coupler and the external cross-sectional dimension of the pin are preferably similar, that of the guide pin being "slightly smaller" than that of the inner surface of the sleeve body. It is not necessary that the cross-sectional areas are the same or similar, so long as the guide pin can fulfill its purpose of directing the sleeve body into the open proximal end of the tube; however, "substantially similar" cross-sectional areas is preferred so as to provide that the sleeve body is movable relative to the guide pin, but that the contact friction between the two may be sufficient to hold the sleeve body in place when the guide pin is held vertically (for example, as illustrated in FIG. 12). In certain embodiments, the external cross-sectional area guide pin is tapered, preferably having a "snugger" fit with the sleeve body at the end furthest from the end being inserted into the tube.

As discussed above, the guide pin may also optionally have attached a mandrel, which fits over and is capable of moving along the guide pin, so that the coupler is press fit or screwed into the open proximal end of the gastrostomy tube using the mandrel. The mandrel may also help press the coupler to the proper depth into the tubing. One or more notches may be cut into the skin flange above the section where the tubing is compressed to help visually verify that the coupler has been properly installed.

Figure 15:
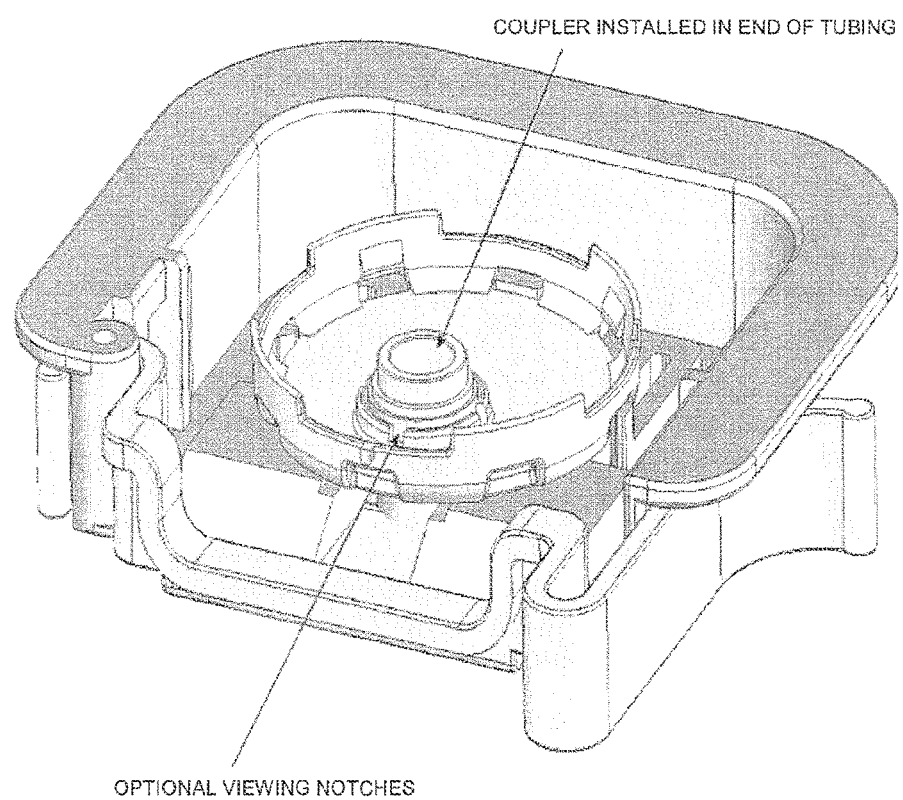
FIG. 15 follows from FIG. 13, after the sliding guide pin/mandrel assembly has been removed, and the coupler remains positioned in the end of the tube.
Figure 16:
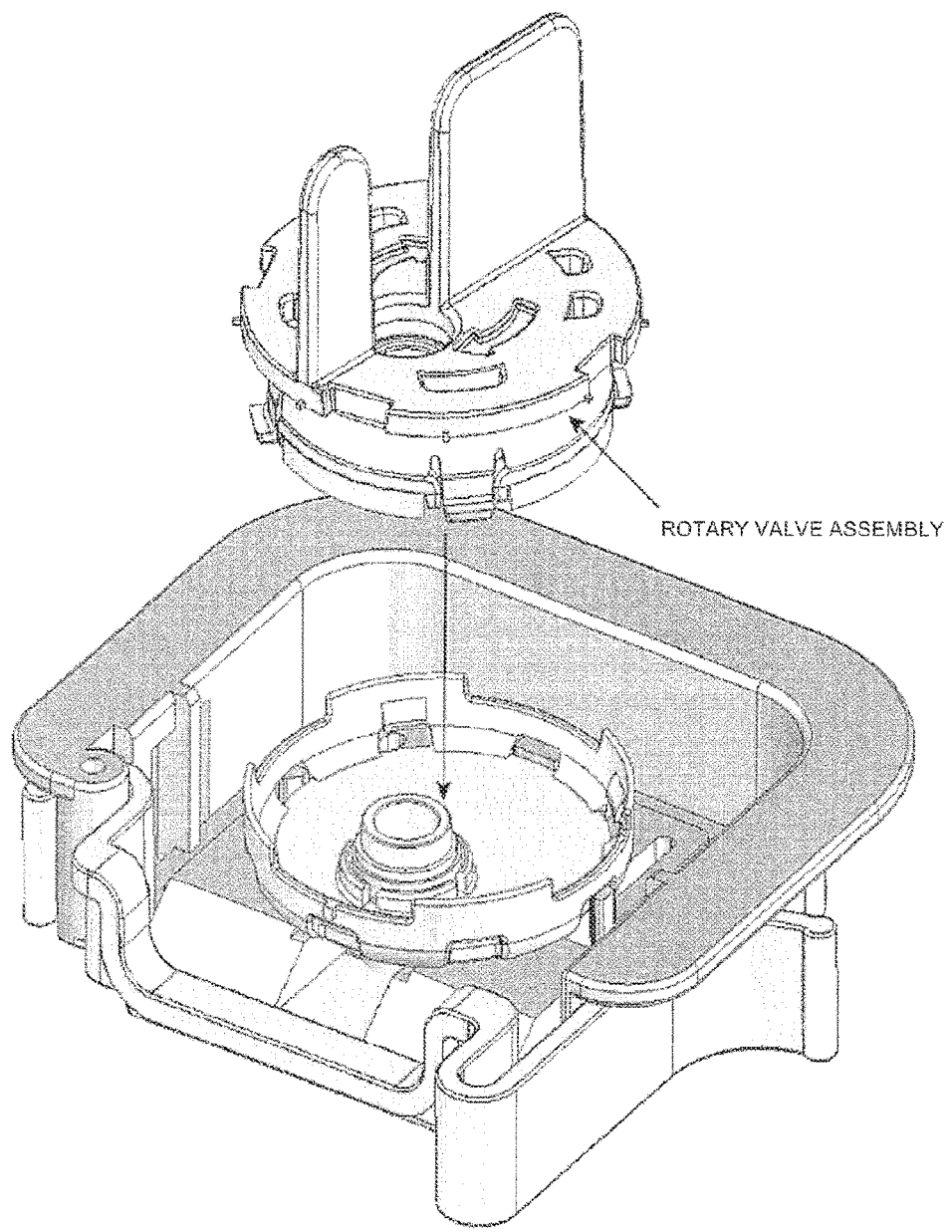
FIG. 16 illustrates one embodied rotary valve assembly positioned to be attached to the skin flange of FIG. 15.
Figure 17:
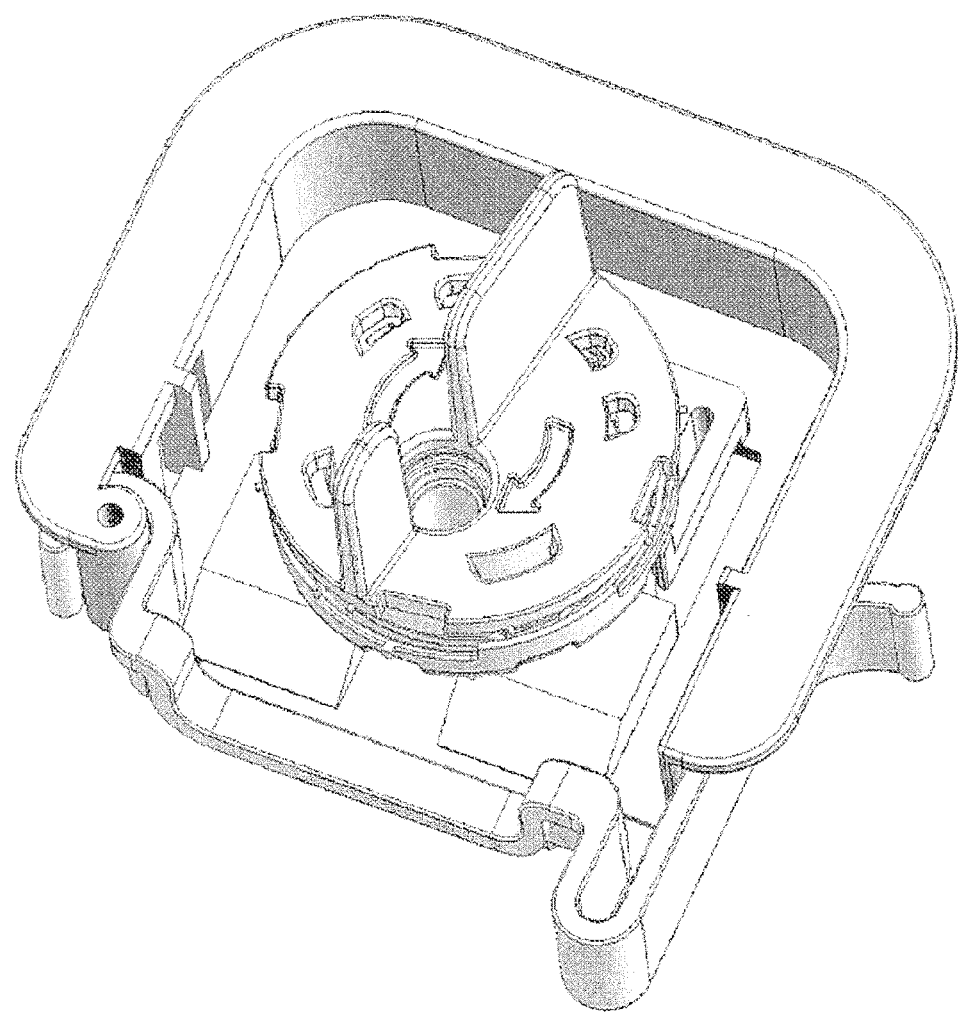
FIG. 17 follows from FIG. 16, and illustrates the rotary valve installed.
Figure 18:
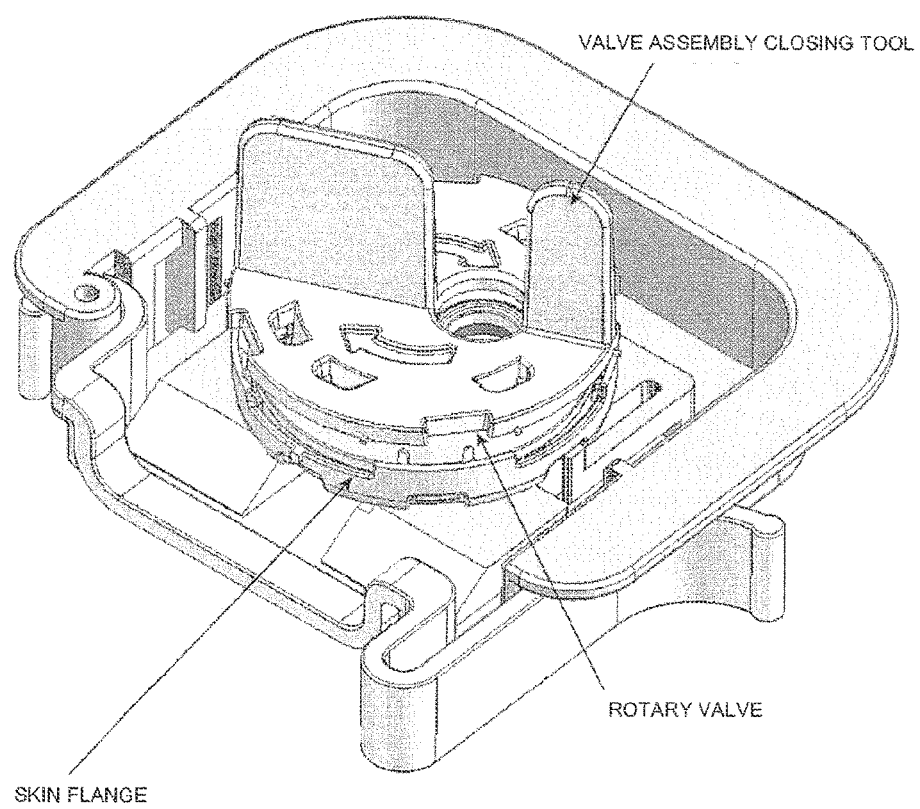
FIG. 18 is another view of the skin port adaptor attached to the installation clamp frame/tray, in which the rotary valve is closed
Figure 19:
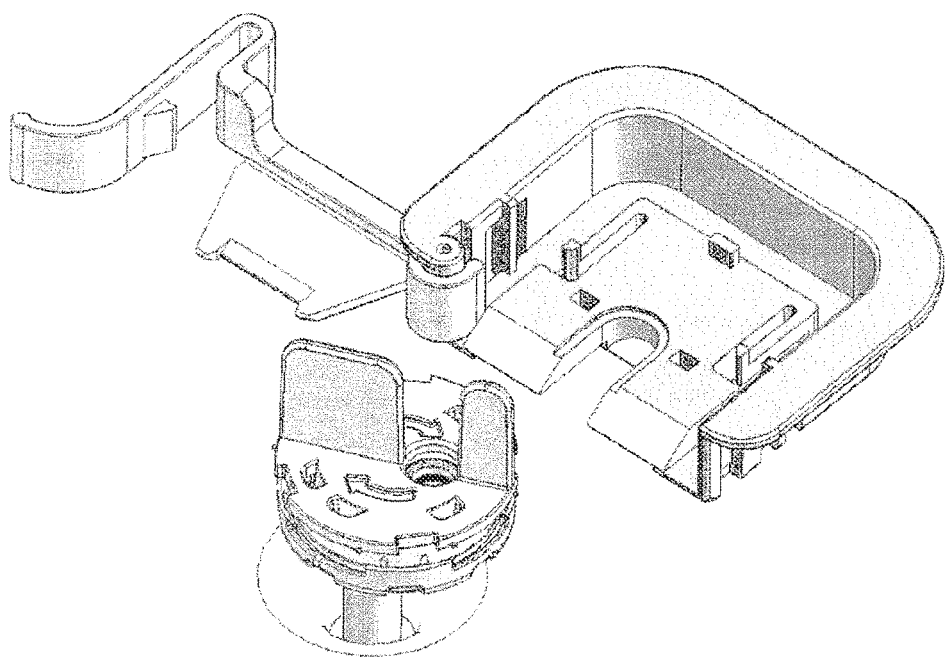
FIG. 19 illustrates the skin port connector attached to the gastrostomy tube after the unclamping of the tube (by opening the latch arm of the movable clamp jaw) and removal of the embodied installation clamp frame/tray

Once the coupler is installed (FIG. 15), securing the tubing to the skin flange, a valve assembly as described in US Patent Application 2011/0082442 can be inserted and attached to the skin flange by barbs on the valve assembly which engage corresponding slots in the skin flange (FIGS. 16-17). Once the valve is closed (FIG. 18), the clamp plate can be unlatched, removed (FIG. 19), and the skin port is ready for use.

Independent embodiments, which may be useful in enabling these methods, include devices (tools) for connecting the skin port connectors described above to a flexible percutaneous gastrostomy tube, each device comprising:

a clamp plate/tray having a base thickness less than about 10 mm, and comprising a tube opening, through which may pass the flexible percutaneous gastrostomy tube, and optionally (a) at least one locator fixture capable of mating with the skin flange so as to hold the skin flange in a position fixed relative to the tube opening; and (b) at least one locator fixture capable of holding a tube cutting tool in a position fixed relative to the tube opening; and optionally an optional movable clamp jaw attached to said clamp plate/tray and configured to be capable of clamping the flexible percutaneous gastrostomy tube which may pass through the clamp plate/tray.

Independent, non-limiting embodiments of various of the device components and methods steps are illustrated in FIGS. 4-19.

The clamp plate/tray can also be used to determine the ideal location of the skin port on the gastrostomy tube before the skin port is installed (FIG. 5). The clamp plate may act as a substitute for the skin port as it is initially clamped onto the tubing while the patient stands to check the fit. If the clamp plate is too close to the skin and creates tension on the internal bolster of the gastrostomy tube in the stomach, the clamp can easily be released and repositioned to improve patient comfort.

The clamp plate/tray provides a working surface that allows connection of the gastrostomy tube to the connector while minimizing the discomfort to the patient (e.g., to prevent twisting or rotating of the tube which exits through and is attached to an external stoma on the patient's abdominal wall). Accordingly, it is desirable that the clamp plate/tray comprises a sufficiently large working area to allow the necessary manual manipulations of peripheral devices and/or couplers. While not limiting, the working area of the clamp plate/tray is conveniently in the range of about 4 in$^2$ to about 10 in$^2$. This working surface of the clamp plate/tray should also be such as to minimize the distance between the skin flange and the patient's skin. While not limiting, the thickness of the clamp plate/tray is conveniently in the range of about 1 mm to about 10 mm, or in the range of about 2 mm to about 8 mm, depending on the strength of the material(s)s of construction. Since the clamp plate/tray may contact the patient's skin in use, it should be made of a non-irritating polymer or metal material.

Additionally, it is convenient, though not required, that the clamp plate/tray comprises walls around this working area, so as to both provide handles for manipulating the plate/tray away from the surface of the patient's skin and to act as a capture surface, for example, should any couplers slide off a guide pin before being inserted into the gastrostomy tube.

Additionally, embodiments of the clamp plate/tray provide for the optional presence of at least one locating fixture which is capable of independently mate with either (a) the skin flange (with which the clamp plate/tray is to be used) so as to hold the skin flange in a position fixed relative to the tube opening; or (b) with a tube cutting tool, so as to hold the cutting tube in a position fixed relative to the a position fixed relative to the tube opening; or (c) both skin flange and tube cutting tool. While each of these skin flange or cutting tool may be held in place by a single locating feature, it is envisioned that a plurality (e.g., 2, 3, 4, 5, or more) of such fixtures are present to accommodate each. So some extent, the walls (a portion thereof) of the clamp plate/tray may serve as one such locating fixture; other exemplary locating fixtures may include at least one of one or more of the following elements: locator pins, protruding nodes, ridges, slots, indentations, cavities, clamps or brackets. The skin flange and cutting tool may also comprise complementary mating features to enable the purpose described.

Non-limiting examples of locating fixtures are seen in FIG. 4 (showing bracketing clamps and posts).

In other embodiments, the clamp plate/tray comprises a clamping device capable of clamping the gastrostomy tube, with which it is to be used. This clamping device may be permanently or semi-permanently affixed to the clamp plate/tray or attachable/detachable thereto. In some embodiments, this clamping device may comprise a screw or otherwise actuated mechanism for pinching the tube closed. In other embodiments, this clamping device may comprise a movable clamp jaw pincer, hinged or otherwise affixed to a clamp plate/tray. One non-limiting example of this latter embodiment is illustrated in FIG. 4.

Figure 6:
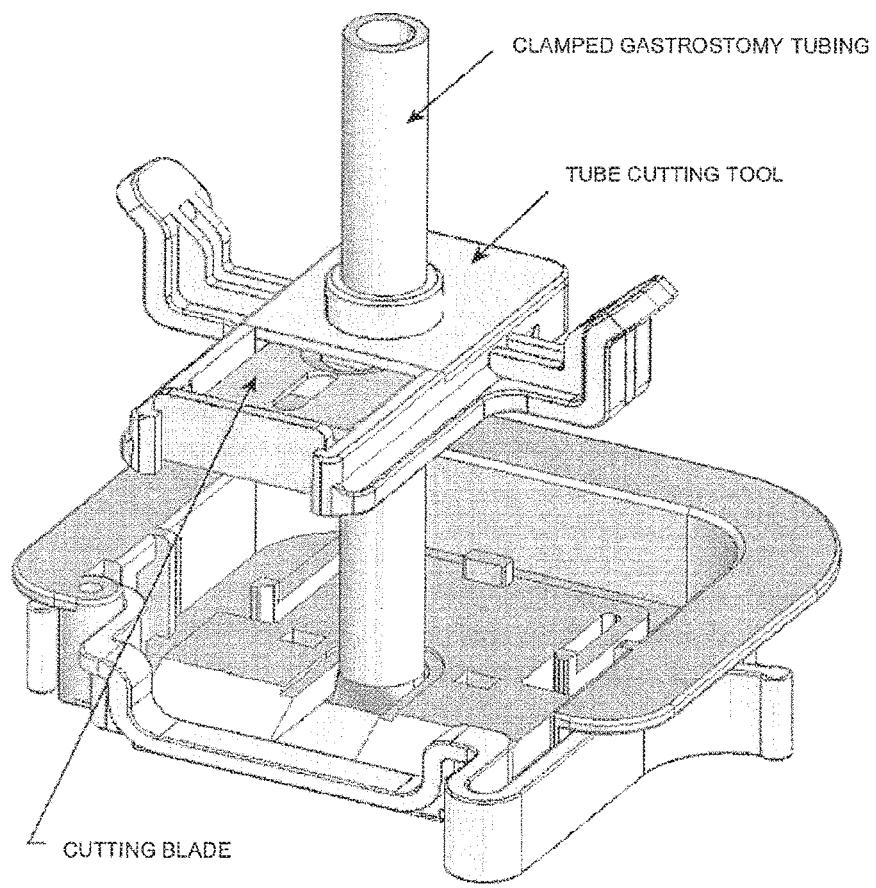
FIG. 6 illustrates one embodiment of a tube cutting tool, as inserted on the clamped gastrostomy tube of FIG. 5.
Figure 7:
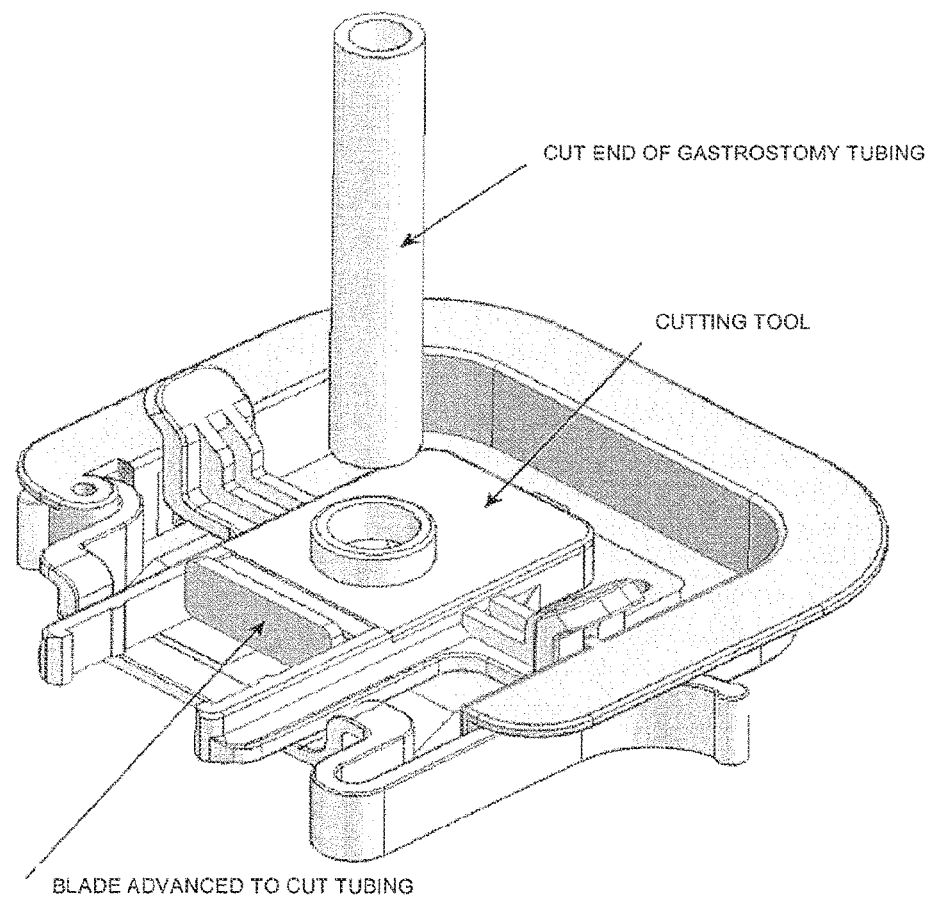
FIG. 7 illustrates one embodiment of a tube cutting tool, positioned on the clamped gastrostomy tube of FIGS. 5 and 6, and positioned as applied on the installing clamp tray of FIGS. 4-6, wherein the cutting blade has cut the clamped gastrostomy tube.
Figure 8:
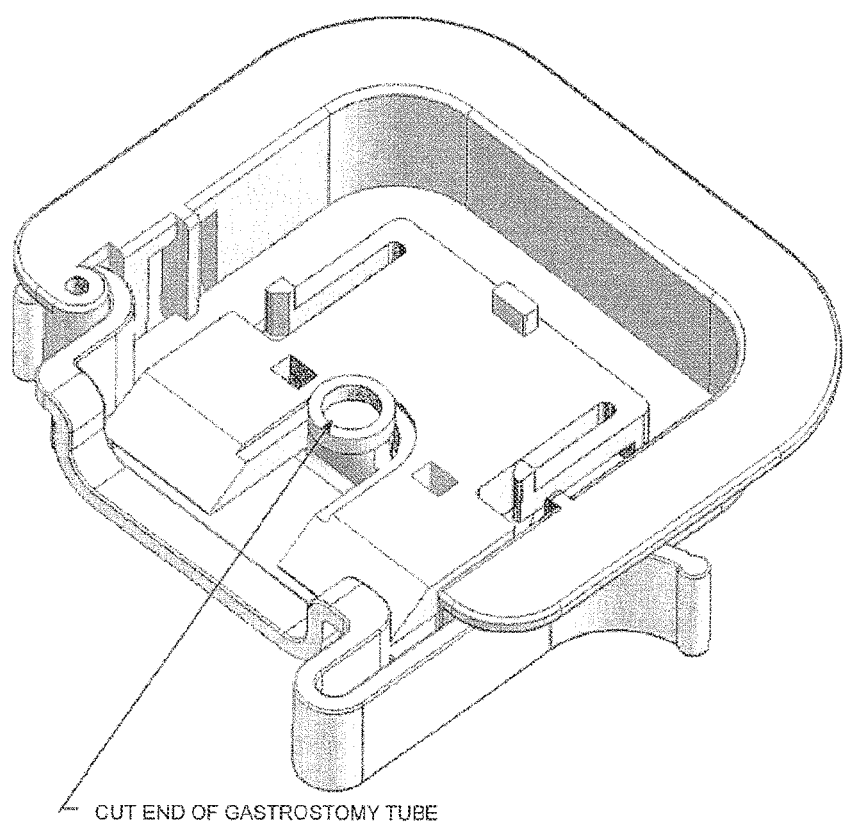
FIG. 8. illustrates one embodiment of the clamped tube cut to length as held by the installing clamp tray of FIGS. 4-7, after the tube cutting tool of FIG. 7 has been removed. The highlighted elements are exemplary locating and/or fixtures as described herein and useful for the positioning of the skin flange.

Independent embodiments include clamp plate/trays comprising the features substantially as shown in FIG. 4, tube cutting tool assemblies comprising features substantially as shown in FIG. 6, sliding guide pin/mandrel combinations comprising features substantially as shown in FIG. 10, and couplers comprising features substantially as shown in FIG. 10. In each case, separate embodiments also include those wherein the features of each component (i.e., clamp plate/tray, tube cutting tool assembly, sliding guide pin/mandrel combination, and coupler) are in at least approximate proportionate size and spatial relationship within and relative to one another.

Additional embodiments provide kits comprising at least two of the following: (a) at least one clamp plate/tray in any configuration described herein; (b) at least one tube cutting tool assembly in any configuration described herein; (c) at least one a sliding guide pin optionally attached to mandrel; and (d) at least one coupler in any configuration described herein. Independent embodiments provide kits com at least two of the following: (a) a clamp plate/tray comprising features substantially as shown in FIG. 4; (b) a tube cutting tool assembly comprising features substantially as shown in FIG. 6; (c) a sliding guide pin/mandrel combination comprising features substantially as shown in FIG. 10; and (d) a coupler comprising features substantially as shown in FIG. 10.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of prior art references which complement the features of the present invention. Additionally, those inventions which derive from the teachings and elements described in U.S. Pat. No. 7,648,479 and U.S. Patent Application Ser. Nos. 2008/0039809, 2011/0082442, 2011/0178480, and 2011/0190719 which are consistent with the teachings and embodiments of the present invention(s) are considered part of the present disclosure and each is incorporated by reference in its entirety for this purpose.

Similarly, it will be appreciated that any described material, feature, or article may be used in combination with any other material, feature, or article.

More generally, the disclosures of each patent, patent application, and publication cited or described in this document are hereby incorporated herein by reference, in their entirety for all purposes.

What is claimed:

1. A skin port connector for use on a flexible percutaneous gastrostomy tube, said flexible percutaneous gastrostomy tube having a tube wall thickness when uncompressed, said skin port connector comprising:
    (a) a skin flange containing a through-hole channel, said through-hole channel having (i) a main inner surface, (ii) a mean cross-sectional dimension and area, (iii) proximal and (iv) distal ends and (v) a center-line axis along the longitudinal axis of the through-hole channel, said through-hole channel further comprising (vi) a circumferential ridge protruding from the main inner surface into the channel of the through-hole at a position within the channel; the circumferential ridge defining a second mean cross-sectional dimension and area that are each less than the mean cross-section dimension and area of the main inner surface; and
    (b) a coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the outer surface of the sleeve body is located (viii) nearer the proximal end of the sleeve body than the distal end and defines (ix) a second outer mean cross-sectional dimension and area;
    wherein at least a portion of the coupler fits within the through-hole channel so that the center-line axes of the through-hole channel and the coupler are substantially coaxial;
    wherein the surface(s) of the circumferential ridge protruding from the main inner surface into the channel of the through-hole and the surface(s) of the circumferential ridge protruding from the outer surface of the sleeve body in closest approach to one another comprise mating surfaces with respect to one another and wherein the circumferential ridge protruding from the main inner surface into the through-hole channel of the skin flange is distally positioned relative to the circumferential ridge protruding from the outer surface of the sleeve body of the coupler;
    wherein the second outer mean cross-sectional area defined by the circumferential ridge protruding from the outer surface of the sleeve body is less than the corresponding mean cross-section area defined by the main inner surface of the through-hole channel but more than the corresponding second mean cross-sectional area defined by the circumferential ridge of the through-hole channel; and
    wherein the difference between the second mean cross-sectional area defined by the circumferential ridge of the through-hole channel and the first outer mean cross-sectional area defined by the sleeve body defines an annulus, said annulus having a width that is less than the thickness of a tube wall of an uncompressed percutaneous gastrostomy tube, such that when the percutaneous gastrostomy tube is coupled to the skin port connector by press fitting the coupler in the annulus, the tube is compressed radially between the through-hole channel and the coupler; and
    said skin port connector further comprising a valve assembly attached to the skin flange, the valve assembly comprising:
    a first platform and having a first thru-hole that passes therethrough, wherein the first platform is adapted for placement adjacent to a patient's skin;
    a second platform having a second thru-hole that passes therethrough; and
    a retainer configured to retain the first platform in proximity to the second platform such that the second platform can be rotated with respect to the first platform between a first position and a second position,
    wherein in the first position the first and second thru-holes align to provide access to a fluid pathway and in the second position the first and second thru-holes offset to provide a fluid tight seal and to prevent access to the fluid pathway.

2. An assembly comprising the skin port connector as described in claim 1 and a flexible percutaneous gastrostomy tube, wherein the flexible percutaneous gastrostomy tube is attached to the skin port connector by a radial compression between the through-hole channel and the coupler resulting from the press-fit coupling of the coupler and the connector.

3. The assembly of claim 2 wherein the flexible percutaneous gastrostomy tube comprises an elastomeric polymer.

4. The assembly of claim 2 wherein the flexible percutaneous gastrostomy tube has a substantially smooth constant inner mean cross-sectional dimension.

5. The connector of claim 1 wherein the wall thickness of the uncompressed percutaneous gastrostomy tube is in the range of about 1 mm to about 3 mm.

6. The connector of claim 1 wherein the length of the through-hole channel or the length of the coupler, or both lengths of the through-hole channel and the coupler is independently in the range of about 4 mm to about 20 mm.

7. The connector of claim 1 wherein the main inner surface of the through-hole channel is cylindrical or tapered.

8. The connector of claim 1 wherein the mating surface of the circumferential ridge protruding from the outer surface of the sleeve body is complementary to the shape(s) of the circumferential ridge of the through-hole channel.

9. The connector of claim 1 wherein the mating surface of the circumferential ridge protruding from the outer surface of the sleeve body and the circumferential ridge of the through-hole channel are orthogonal to the sleeve body and the main inner surface of through-hole body, respectively.

10. The connector of claim 1 wherein the difference between the second mean cross-sectional dimension provided by the circumferential ridge of the through-hole channel and the mean cross-section dimension of the main inner surface is in the range of about 2 mm to about 8 mm.

11. The connector of claim 1 wherein the difference between the first outer mean cross-sectional dimension defined by the outer surface of the sleeve body and the second outer mean cross-sectional dimension provided by the circumferential ridge protruding from the outer surface of the sleeve body is in the range of about 3 mm to about 10 mm.

12. The connector of claim 1 wherein the circumferential ridge protruding from the outer surface of the sleeve body is located within a distance in the range of about 0.5 mm to about 3 mm of the proximal end of the sleeve body.

13. The connector of claim 1 wherein distal end of the sleeve body is chamfered.

14. The connector of claim 1 wherein the inner surface of the sleeve body is substantially smooth.

15. The connector of claim 1, wherein the inner mean cross-sectional dimension of the sleeve body is substantially similar to the inner mean cross-sectional dimension of the uncompressed percutaneous gastrostomy tube.

16. The connector of claim 1, wherein the width of the annulus, defined by the difference between the second mean cross-sectional area defined by the circumferential ridge of the through-hole channel and the first outer mean cross-sectional area defined by the sleeve body defines an annulus, is in the range of about 5% to about 90% of the thickness of the tube wall of the uncompressed percutaneous gastrostomy tube used or to be used.

17. A method of connecting a skin port connector to a flexible percutaneous gastrostomy tube that passes from and through a patient's stomach, and exits through an external stoma on the patient's abdominal wall, said flexible percutaneous gastrostomy tube having a distal end within the patient's stomach and a proximal end to be connected outside of the patient's body, wherein the proximal end of the flexible percutaneous gastrostomy tube, outside of the patient's body has an inner cross-sectional dimension, an outer cross-sectional dimension, and an uncompressed tube wall thickness, said method comprising:
  (a) clamping the flexible percutaneous gastrostomy tube between the external stoma and the proximal end of the flexible percutaneous gastrostomy tube to be connected, so as to substantially prevent the flow of material out of the stomach;
  (b) passing the gastrostomy tube through a clamp plate/tray having an area that contacts the patient's skin;
  (c) locating the proximal end of the flexible percutaneous gastrostomy tube within a through-hole channel of a skin flange at a pre-determined height relative to the through-hole channel, said through-hole channel having (i) a main inner surface, (ii) a mean cross-sectional dimension and area, (iii) proximal and (iv) distal ends and (v) a center-line axis along the longitudinal axis of the channel, said through-hole channel further comprising (vi) a circumferential ridge protruding from the main inner surface into the channel of the through-hole at a position within the channel; the circumferential ridge protruding into the channel of the through hole defining a second mean cross-sectional dimension and area that are each less than the mean cross-section dimension and area of the main inner surface; and
  (d) press fitting a coupler into the open proximal end of the flexible percutaneous gastrostomy tube, said coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the outer surface of the sleeve body is located (viii) nearer the proximal end of the sleeve body than the distal end and defines (ix) a second outer mean cross-sectional dimension and area;
  so that at least a portion of the coupler fits within the through-hole channel and the center-line axes of the through-hole channel and the coupler are substantially coaxial;
  wherein the clamp plate/tray is capable of distributing any pressure associated with inserting the coupler over the area of the clamp plate/tray that contacts the patient's skin;
  wherein the surface(s) of the circumferential ridge protruding from the main inner surface into the channel of the through-hole and the surface(s) of the circumferential ridge protruding from the outer surface of the sleeve body in closest approach to one another comprise mating surfaces with respect to one another and wherein the circumferential ridge protruding from the main inner surface into the through-hole channel of the skin flange is distally positioned relative to the circumferential ridge protruding from the outer surface of the sleeve body of the coupler;
  wherein the second outer mean cross-sectional area defined by the circumferential ridge protruding from the outer surface of the sleeve body is less than the corresponding mean cross-section area defined by the main inner surface of the through-hole channel but more than the corresponding second mean cross-sectional area defined by the circumferential ridge of the through-hole channel; and
  wherein the difference between the second mean cross-sectional area defined by the circumferential ridge of the through-hole channel and the first outer mean cross-sectional area defined by the sleeve body defines an annulus, said annulus having a width that is less than the thickness of the tube wall of the uncompressed percutaneous gastrostomy tube;
  so as to compress the tube radially between the through-hole channel and the coupler;
  wherein the coupler is press fit into the open proximal end of the flexible percutaneous gastrostomy tube to a distance defined by further inability of the circumferential ridge protruding from the outer surface of the sleeve body to pass beyond the circumferential ridge protruding from the main inner surface into the channel of the through-hole in the presence of the compressed percutaneous gastrostomy tube; and
  wherein the coupler is guided into the open proximal end of the flexible percutaneous gastrostomy tube using a guide pin, said guide pin having an external cross-sectional area substantially similar to the inner cross-sectional area of the coupler, said coupler being slidably detachable from the guide pin.

18. The method of claim 17, further comprising attaching a valve assembly to the skin flange, such that the valve assembly seals the proximal end of the tube, thereby preventing the flow of material out of the stomach on release of the clamping.

19. The method of claim 17, wherein the clamping comprises collapsing the flexible percutaneous gastrostomy tube using a movable clamp jaw pincer that is connected to a frame capable of attaching and/or holding a tube cutting tool and/or the skin flange in a substantially fixed and pre-specified position relative to the frame.

20. The method of claim 17, further comprising trimming the proximal end of the flexible percutaneous gastrostomy tube at a pre-set distance from the stoma before locating the proximal end of the flexible percutaneous gastrostomy tube within the through-hole channel of the skin flange at a pre-determined height relative to the through-hole channel.

21. The method of claim 17, wherein the external cross-sectional area of the guide pin is tapered.

22. The method of claim 17, wherein the coupler is press fit into the open proximal end of the flexible percutaneous gastrostomy tube using a mandrel, which fits over and is capable of moving along the guide pin.

23. A device for connecting a skin port connector for use on a flexible percutaneous gastrostomy tube to the flexible percutaneous gastrostomy tube, said flexible percutaneous gastrostomy tube having a tube wall thickness when uncompressed, said skin port connector comprising:
(a) a skin flange containing a through-hole channel, said through-hole channel having (i) a main inner surface, (ii) a mean cross-sectional dimension and area, (iii) proximal and (iv) distal ends and (v) a center-line axis along the longitudinal axis of the through-hole channel, said through-hole channel further comprising (vi) a circumferential ridge protruding from the main inner surface into the channel of the through-hole at a position within the channel; the circumferential ridge defining a second mean cross-sectional dimension and area that are each less than the mean cross-section dimension and area of the main inner surface; and
(b) a coupler comprising a sleeve body having a bore therethrough and a circumferential ridge protruding from the outer surface of the sleeve body, said coupler having (i) proximal and (ii) distal ends and (iii) a center-line axis coincidental with the longitudinal axis of the bore, said sleeve body having (iv) inner and (v) outer surfaces and (vi) an inner mean cross-sectional dimension and area defined by the inner surface and (vii) a first outer mean cross-sectional dimension and area defined by the outer surface of the sleeve body, and wherein the circumferential ridge protruding from the outer surface of the sleeve body is located (viii) nearer the proximal end of the sleeve body than the distal end and defines (ix) a second outer mean cross-sectional dimension and area;
wherein at least a portion of the coupler fits within the through-hole channel so that the center-line axes of the through-hole channel and the coupler are substantially coaxial;
wherein the surface(s) of the circumferential ridge protruding from the main inner surface into the channel of the through-hole and the surface(s) of the circumferential ridge protruding from the outer surface of the sleeve body in closest approach to one another comprise mating surfaces with respect to one another and wherein the circumferential ridge protruding from the main inner surface into the through-hole channel of the skin flange is distally positioned relative to the circumferential ridge protruding from the outer surface of the sleeve body of the coupler;
wherein the second outer mean cross-sectional area defined by the circumferential ridge protruding from the outer surface of the sleeve body is less than the corresponding mean cross-section area defined by the main inner surface of the through-hole channel but more than the corresponding second mean cross-sectional area defined by the circumferential ridge of the through-hole channel; and
wherein the difference between the second mean cross-sectional area defined by the circumferential ridge of the through-hole channel and the first outer mean cross-sectional area defined by the sleeve body defines an annulus, said annulus having a width that is less than the thickness of a tube wall of an uncompressed percutaneous gastrostomy tube, such that when the percutaneous gastrostomy tube is coupled to the skin port connector by press fitting the coupler in the annulus, the tube is compressed radially between the through-hole channel and the coupler, said device comprising:
a clamp plate/tray having a base thickness less than about 10 mm, and comprising a tube opening, through which may pass the flexible percutaneous gastrostomy tube;
a movable clamp jaw attached to said clamp plate/tray and configured to reversibly clamp the flexible percutaneous gastrostomy tube which may pass through the clamp plate/tray, such that when clamped, the position of the flexible percutaneous gastrostomy tube opening is fixed with respect to the position of the clamp plate/tray; and
an attachable coupler installation tool comprising a sliding guide pin insertable into the flexible percutaneous gastrostomy tube opening so as to be capable of delivering the coupler into the flexible percutaneous gastrostomy tube opening.

24. The device of claim 23 wherein the clamp plate/tray has a base thickness in the range of about 1 mm to about 8 mm, the device further comprising at least one of (a) at least one locator fixture capable of holding the skin flange in a position fixed relative to the tube opening; or (b) at least one locator fixture capable of holding a tube cutting tool in a position fixed relative to the a position fixed relative to the tube opening.

25. The device of claim 24, further comprising at least one locator fixture capable of mating with the skin flange so as to hold the skin flange in a position fixed relative to the tube opening.

26. The device of claim 23, wherein the movable clamp jaw is hinged to the fixed clamp/tray plate.

27. The device of claim 23, further comprising at least one locator fixture capable of holding a tube cutting tool in a position fixed relative to the tube opening.

* * * * *